US010106802B2

(12) United States Patent
Cheng et al.

(10) Patent No.: US 10,106,802 B2
(45) Date of Patent: Oct. 23, 2018

(54) POLYNUCLEOTIDE SEQUENCES FROM RHODOSPORIDIUM AND RHODOTORULA AND USE THEREOF

(71) Applicant: TEMASEK LIFE SCIENCES LABORATORY LIMITED, Singapore (SG)

(72) Inventors: Hsin I. Cheng, Singapore (SG); Ni Peng, Singapore (SG); Lianghui Ji, Singapore (SG)

(73) Assignee: TEMASEK LIFE SCIENCES LABORATORY LIMITED, Singapore (SG)

( * ) Notice: Subject to any disclaimer, the term of this patent is extended or adjusted under 35 U.S.C. 154(b) by 0 days.

(21) Appl. No.: 14/773,836

(22) PCT Filed: Mar. 10, 2014

(86) PCT No.: PCT/SG2014/000114
§ 371 (c)(1),
(2) Date: Sep. 9, 2015

(87) PCT Pub. No.: WO2014/142747
PCT Pub. Date: Sep. 18, 2014

(65) Prior Publication Data
US 2016/0032296 A1    Feb. 4, 2016

Related U.S. Application Data

(60) Provisional application No. 61/782,832, filed on Mar. 14, 2013.

(51) Int. Cl.
*C12N 15/80* (2006.01)
*C07K 14/37* (2006.01)
*C12P 21/02* (2006.01)

(52) U.S. Cl.
CPC .............. *C12N 15/80* (2013.01); *C07K 14/37* (2013.01); *C12P 21/02* (2013.01)

(58) Field of Classification Search
None
See application file for complete search history.

(56) References Cited

U.S. PATENT DOCUMENTS

2006/0057690 A1    3/2006   Xue et al.

FOREIGN PATENT DOCUMENTS

| CN | 102268432 B | 3/2013 |
| WO | 2005003310 A2 | 1/2005 |
| WO | 2005049805 A2 | 6/2005 |
| WO | 2012169969 A1 | 12/2012 |

OTHER PUBLICATIONS

Riethoven, Methods in Molecular Biology vol. 674 (2010) pp. 33-42, "Regulatory regions in DNA: promoters, enhancers, silencers, and insulators.".*
Liu, Y., et al. "Characterization of Glyceraldehyde-3-Phosphate Dehydrogenase Gene RiGPDI and Development of Genetic Transformation Method by Dominant Selection in Oleaginous Yeast Rhodosporidium Toruloides," Applied Microbiology Biotechnology, 2013, vol. 97 (ePub Jun. 22, 2012), pp. 719-729.
Abbott, E.P., et al., "Overcoming Recalcitrant Transformation and Gene Manipulation in PucciniomycotinaYeast," Applied Microbiology Biotechnology, 2013, vol. 97 (ePub Nov. 14, 2012), pp. 283-295.
Doyle, C.E. et al., "Ustilago Maydis Transcript Features Identified Through Full-Length cDNA Analysis," Molecular Genetic Genomics, 2011, vol. 286, pp. 145-159.
International Search Report dated Jun. 11, 2014, International Application No. PCT/SG2014/000114, filed Mar. 10, 2014, Applicant: Temasek Life Sciences Laboratory Limited, 7 pages.
Search Report dated Oct. 28, 2016 issued in counterpart European Application No. 14765272.1 (6 pages).
Tyler Avis et al. "Usefulness of Heterologous Promoters in the Pseudozyma flocculosa Gene Expression System", Bioscience, Biotechnology, and Biochemistry, Feb. 2008, pp. 456-462, vol. 72, No. 2, XP055120692.
Bertrand Neveu et al. "Cloning of the glyceraldehyde-3-phosphate dehydrogenase gene from Pseudozyma flocculosa and functionality of its promoter in two *Pseudozyma* species", Antonie van Leeuwenhoek Kluwer Academic Publishers, Mar. 2007, pp. 245-255 vol. 92, No. 2, XP019523318.
Bertrand Neveu et al. "The Pseudozyma flocculosa actin promoter allows the strong expression of a recombinant protein in the *Pseudozyma* species", Applied Microbiology Biotechnology, Jan. 2007, pp. 1300-1307, vol. 74, No. 6, XP019513616.
Supplementary Search Report dated Mar. 31, 2017 issued in European Application No. 14765272.1 (25 pages).
Chinese Office Action issued in Application No. 201480024515.3 dated Mar. 28, 2018, with English Translation, 17 pages.
Indonesian Office Action issued in Application No. P00201506471 dated Jul. 17, 2018, with English Summary, 4 pages.
Malaysian Office Action issued in Application No. PI 2015002329 dated Aug. 30, 2018, 4 pages.

* cited by examiner

*Primary Examiner* — James S Ketter
(74) *Attorney, Agent, or Firm* — Rothwell, Figg, Ernst & Manbeck, P.C.

(57) ABSTRACT

The present invention relates to the application of isolated promoters and synthetic constructs for efficient production of genetically modified cells in a species selected from the Pucciniomycotina and Ustilaginomycotina subphyla, in particular, species selected from the *Rhodosporidium, Rhodotourla, Sporobolomyces* or *Pseudozyma* genus.

13 Claims, 5 Drawing Sheets
Specification includes a Sequence Listing.

SEQUENCE LISTING

```
<160> NUMBER OF SEQ ID NOS: 42

<210> SEQ ID NO 1
<211> LENGTH: 1027
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1022)..(1027)
<223> OTHER INFORMATION: NcoI cloning site

<400> SEQUENCE: 1
ggtaccgtgc gagaagaagc gaggcacgcg aagcggtaga agcaatgaag cgaggcgaga      60
gcgagagagg cagggcttca gccatgtcca gctgatcggc tgtaacgtcg cgccgggcca     120
gtctgttgaa tttgttgcgt cgcctgagcg taatagaagt gcagtagtct actccgcatg     180
ccgagaacgt cgaagagcgc gaagtaggga gtcgagggaa gcgagggtgg caaacacagc     240
aacgacaagc ggttccgctt cgctcaaaag ctcgttgacg ttgttttgac gttttgaaga     300
cagtacaaca gcagcaagag gcgtgcgaag cgttggtggc gagagcagcg acaaggaggg     360
aggaatgagg gagtggtggc gagggctcgc aaacgggcgt acgcctcgaa tggagacgtg     420
cgagtcgttc ttcgacgtcc gagggatgcc gagcgccgag acggagcacg caacgagcga     480
gaggagagca gccgcgcaag gtgattcgag tggcgcaagc ggaggacgac gaggagacgg     540
acgagggagg aggagggatg gcgagcgagc atcggacggc ggggcgcgag agacggcgtg     600
aggagccggg tgtggagagt ttgaggaggc gcgggatgcg aagtggctgg gtgtgcggag     660
tgagcggtgg caaagagcgc acttagagtc tagagcgagg cagtagtagt agagctgtat     720
gaatgaatac aaagtgtgaa tacaacagtt tgtaatgcga ttctgagctt ggacgtgtgc     780
```

| | |
|---|---|
| gcgcgagagg gcgacttgca agccagcgcc cgctcgctct tcttccttct gcacctcgcg | 840 |
| tcaaccctcg catctcacac ctacactcgc attcaaagtg cgtacactct cccacgacac | 900 |
| acggggacgg cgcacaccac cgcgcgtcgc ttgaacggcg tcgccacttc gagccgtcac | 960 |
| tgacttcgtc ctcgtcctcc ctcctctact ctcttgtact gtactgtgta ctgggggga | 1020 |
| accatgg | 1027 |

```
<210> SEQ ID NO 2
<211> LENGTH: 956
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (951)..(956)
<223> OTHER INFORMATION: NcoI cloning site

<400> SEQUENCE: 2
```

| | |
|---|---|
| ggtacccatg ctgctgctgc ccctcaaagg tcctctcgtc cacgtccgac gagtctggac | 60 |
| agctttcaca gtcccgagag tgcaagagcg aggcgggctc acggttccgc aaaggagcgc | 120 |
| gaggtccgac cgccggccgg tctccttgcc cgcctcgcct cacctcctct tgcagcaggt | 180 |
| tcacctcttc gaggtcactc gatcgctcgc agcgatgcgc aggtacaagt acgctaggcg | 240 |
| agagcgtcga aagcggggtt ctgcgaggga ctggacgctg cagagcgcgg tcgagagagg | 300 |
| ctcgagtggc gctttgaccg ctcgacgcaa ggcatgcgct cctccgtttg agctcgcaga | 360 |
| tactgccgtg cgaagacgag cataggctgt ggctgcggta gcaaggagcc ggcgagagaa | 420 |
| agctgtgctc gagcaggacg agagacggtc cgcgcgcttg agaaggtcga ggtgaggcgt | 480 |
| cgcaaccggg ttggatctcg attctcggcg aactacggct tcggcgaggg ccaaagcgac | 540 |
| ggcaggccgc gcaagctggc caggcgagag cgcgagagtc gcgagctgaa gcggcgcgg | 600 |
| ggtagagcaa gctggggaag cgagagaggg agagagagag agtgaggggg tggcgaggtg | 660 |
| gagacgaggc gagcggttgg cttgcgcgcg cgcgagaggg atcgaggcga gaggcgagcc | 720 |
| ccgagagtgg aaggaaggac gaggaaacct gcgtgcggag gcgccgcgcg cgcgtgccac | 780 |
| ctggctgagc acgggcccga gcttgaggga gctgggggcg cgcgagcgag acgagggcag | 840 |
| ggcgagcccg cgcgtggcgg ccgcctcgca acccaaggct cgccctggcc gccgctcttg | 900 |
| ctctctttcc tccaccttcg cgtctcacca ctcgaatctc acttcatcca ccatgg | 956 |

```
<210> SEQ ID NO 3
<211> LENGTH: 1474
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1469)..(1474)
<223> OTHER INFORMATION: NcoI cloning site

<400> SEQUENCE: 3
```

| | |
|---|---|
| ggtacccaaa gggagaggag cgggcggagg atggtggtgc cggacagggc gagagggaag | 60 |
| gtcgagggag agatgggagc gcgaaaggtc gaggcgggga gagggagggt ggggtcggga | 120 |
| ccaaggggc agagaggctc acaaggacgg aggagcttac tccgccttga ccttgcgggt | 180 |

-continued

| | |
|---|---|
| ggcggtggtg ccctcgcgga agctgcggcg cgaggaaggt cgtcagggcc gggcccaggg | 240 |
| gaggaacgag gacggcgacg acgacgcacc cgttcttgaa gcggcgcgag acgcccttca | 300 |
| ggtgctgcat gcggccagtg ccagtggtgt ggcggcgctt ggccttctgt ccccactcgt | 360 |
| ctgcgcggcg agggagaagg cgaggtgagc acgacggcgc gcgagggccg gacgaggctg | 420 |
| agaggggggac gcacacgagc ggagcttggc cgcggggtag ccgcacgaag cgcacgactt | 480 |
| gtgctgcttg tggaacgagc ggcggccgca gcgacggcac agactgtggg accacgaggg | 540 |
| tcaaccgggt gctcgcgaga caggagcgcg gcttgtctcg aagcacgggc aaagagagcg | 600 |
| ttggacgcac gtgtgactct tggtgtggcg gagaccgaac gaggtggtac ccttcgtctg | 660 |
| tggggcgcaa ggaggagtgg gtcagcgtcg ggcctcgagg cgcctgggtc gtcgacctcg | 720 |
| cccgctcccg atcctcgcgc cgtcctgctc ctcctctctc caaccctgcg acgtgttgcg | 780 |
| gcagcagcag cttgctggga catgtgggga gggcggcaag gcgaggggag gtcgaggtgc | 840 |
| gaatgtgggt ggtcgcgctt ggcggggcag catgtcgtcg cggcctcgag ccgggcgggc | 900 |
| gacctggtgg ccgggtcgag cgagaggcgt gggagggagt ggcgcaaatg gcgtgcgctc | 960 |
| agaggcgggt tgtcgaggcg tcgaggcgga cgaggtcgag gaggtcgagg tgggaagctg | 1020 |
| ctgctgctgc tcgggcgtcg tcgccgcgtc ccgagtgccc cgtgcgcgcc cctgctgccg | 1080 |
| ctccttgggc cgtcctggtc ccacctgccc gtgccgtcct ccacgagagc gcgagtgggg | 1140 |
| ctgtgcgccg ggttgcgctc caactttgcg agagagcgag gacgggggca tggctcgctc | 1200 |
| gccggcctcg ggtcgttcga ggggtcgggg gcgggttgcg ggagggtggt gcgaggtggc | 1260 |
| gggcttacca ttgtcgcgtc ggagaggggg gtttggcctg cgagaagacg aggagacgag | 1320 |
| aggccggggg aggcgaggcg gcgaggcggc gagacggctc ggaccaagcg cgcgccgcca | 1380 |
| aagtctgcct cgccgctcgc gctcgcctcc ctcttgctct ccacctcctc ctaggaccac | 1440 |
| aaaggcaccc ttgtgtaggc gtaggtcacc atgg | 1474 |

<210> SEQ ID NO 4
<211> LENGTH: 1327
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1322)..(1327)
<223> OTHER INFORMATION: BspHI cloning site

<400> SEQUENCE: 4

| | |
|---|---|
| ggtacctgag cgggcgagcc gcgagcgagg agcgttgagg aggaagggag ggagggagga | 60 |
| gggagaggga gggagggac ccccatcttt ctattcattc acaaagacga cggtgcggag | 120 |
| gggtccctcg agtgtttggg ctgggcttcg gagtctcgta gcgagcaagt agtgtttctc | 180 |
| tccgtttcga cagctcgtat tgtcatttct tgttcattgt cgtttccggc gactgcaggt | 240 |
| acgctgattt tcggcggaga cgacaagcac gtgggttgtg agcagcgagt tgagcaagaa | 300 |
| aaagcggacg aaggccctcg tcgggggctt caagtcaaga ttctgcgag attctgcgag | 360 |
| agactgcaag cgttgaacct gttgagatct cgtcggacga cagcacagtg tccgtctcgc | 420 |
| tcaatgcgat aggaagcgag agagaggagg aggatatcgg aggaaggcgt gtttgcgttc | 480 |
| gctccaggcg tcgcaagatc cggcgtagag cacaatcgtc gttggttcga cgtttgtagt | 540 |
| tcgtcacgag tgagggcgaa gcctggcaag caaagaaggg gacgagcgac tcggcagcta | 600 |

```
tcgctggagg agggcgactt tgtggcccgt ttccgtcgag ctcgacgcga gtgagcgcag    660
ggtcggtccg aaccgatgcc atggacgcag tgagcgaggc cggatgtgcg atgctgtttc    720
aagcgagcga aggaagggag aaagcgagcg agaggtcctc ctcctgtctt cctcacgcct    780
tccgaaggcc gacaagaggc gtagacgtcg acgagtcaac ggtttgacgt cgctcaggcc    840
tgtagcgggt cgtcggaagc tgggaaagag aggaaccaac gagtaacaag cgcgagagtc    900
tcctcaaggc ggacaattgc ctcgcttcgg tcccggtcga gctcttccag taccagcgag    960
ggcgaaagtc gtcgatgcgt gcgcatccaa ggccaagcgt cgcagtcgag aagagcgaga   1020
gtgaagcgag tgaagcggga gagtgagagc gggtaatccg cgtacttacg agtgggttgt   1080
attccttctt gtaatggcag attacctcga ttggccacgt cacgttccgg gagtgcccgg   1140
gcgtgggcaa aagggcgagc gcggcgcctc tctctcttgc ttcctcagca gagcagctct   1200
cccctcgagt acgtcgacgg gctcactaca gctagcaaca gcaaggctac cacgccagct   1260
acacgccagc tcacccaact cacaccgctc gttgtcgccg cgcgccgcag gaaaactttg   1320
ttcagtc                                                              1327

<210> SEQ ID NO 5
<211> LENGTH: 1509
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1504)..(1509)
<223> OTHER INFORMATION: NcoI cloning site

<400> SEQUENCE: 5
ggtaccgctc atcatcgagc gagggcagca gcgacctgcg gactggccga agaacttccc     60
cggccagcgc ttcgaggaca aggacattcg cacgcctcgc tctcagtggc ggtacatcaa    120
gctggcgacc acagacgacc tctcgccgac tgaggagaac acgacgtcct gcgccgtccg    180
gtacggcgag gactcgcagc tcgccatctt ccacgttccc ggcaagggt  acttctgcac    240 gcagcagatg tgtcctcgtg cgtcgcgcct gctctctctt tctttatttg ctggctgact    300
cgtgctgact cgcccgaaac ctcagacaag cgcgccttca tcctcgagca tggcatcgtc    360
tcggacgacg ggagtggcca cctctacgtc tcctgcccgc tccacaagcg caacttccgc    420
ctcgacaacg gcgactgcct caacgacgag gagtacaaga tcctcgcgtt tgatgtcaag    480
gaggagaacg gcgacttgct cgttcaggtt cctccgcctg acgagctcga cgctttgatt    540
gggtgcgtct cgcttagccc tctctcaaag acctgagctg acccttctga ttgtccgcag    600
ctcgtcgaag tggatggtgc gcaaagcgac cgccgaagcc ttcggtcgca acgcagcgac    660
agccatcgag tgcgtcccct ccaagcttct gttttccgcg cgcacactag gctgacgaca    720
agtctctgca ggatcgtcgg accgtcaggc gaggttgacg aggacaagaa ggcagcggga    780
acagagtgcg gcgaagcgga taagtcttgc gggacgcaca agctcgagtg gtgattcttg    840
cgggtccgtc acagccaatg tatctatctc tagatgtcct tctcgggtat atcagttgtt    900
cgtgcatcgt agacgtcgtt tagcagctct cgttcagcca cttgcgaagg cccgcttctt    960
cgacgacaag gacggcttcg cttcctttac ctcgtcgtct gagcgttctc aagggaccct   1020 cctacgcccct tcttcgcaca ggagcggccg acgaggcagc cttgctggct tatcgtcgct   1080
tccgcctttc atgctcgagc aagtcctcct gcgagtgtcc cgacgtcggc ccgccttgcc   1140
```

| | |
|---|---|
| caaggtcgcc gactgtccta tcgcgacact gcgaatgcac tgctgtccgc gccggagact | 1200 |
| gtgcggcgcg aattgagggc aaagtcgtgc atttgcgaaa cggtatccgc tcgaagggcc | 1260 |
| cacgatagac ctccaccggc ctcaaacttg gcgacagggt cgcttccgac ggcggacagc | 1320 |
| aagttaggct ttggcgtcgt cgctgcgatc cgctttgcgg gacccttat cgcgactgcc | 1380 |
| ggattcgatt ggcgatatct ctcgctcgct ggcctcgctg gacagctgga cagtctctgc | 1440 |
| agcgtcgaag cgacgtcgat aaagtcagcg acgtcctcgc gaaccaagaa gaatcacccg | 1500 |
| ccgccatgg | 1509 |

<210> SEQ ID NO 6
<211> LENGTH: 1606
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1601)..(1606)
<223> OTHER INFORMATION: NcoI cloning site

<400> SEQUENCE: 6

| | |
|---|---|
| actagtcgcc agggaacgca gagaaggcgg gacgagcgag ggtgagtcgc gcaagtcgac | 60 |
| gaagaagccg aggtcaacgt cgagggttgt caagttctgg cagacggaca gcagccacac | 120 |
| taatcgctgc cgacttctga tgcatcgtcg cgcgggtgtc agctcctagc cgtggaagga | 180 |
| ggaagccagg acgttctcac cgggcgacgc attgcttgtg ccagacctcg aggcgagctt | 240 |
| gtcgcgtcga aagaccggcg acctcgtccg gctcaaattc cagcccgagt gattgccctg | 300 |
| acaacaaagg cgaaaagctg aagccggtac caaaggtcgg tccatcgaaa gtcgcgctcc | 360 |
| gaagactggc gtcgacggat ctgaccatcg ctgcccctcc tgcgtctgct ttgaggcacc | 420 |
| ttacagcctc ctcgtctcgt tcggagcctc cgcatccgct tggcaggacc acctcgcgac | 480 |
| cagtgacctc ccttgcgatg gctcgccaag tcttgcatac tccggcgacg ttgcggaagg | 540 |
| cgcaggtggg gcaggagatg cggagcgttg tgaactgtcc gttgacgagg agtgtcggcg | 600 |
| aaagaagggc ggtggtgaga gagtaggtga ggatcttgag gaggagttca ggaggaagtg | 660 |
| aggaaaggtc tgccggtgac tggtaaggct gaagcatgat ggcgagtgta gccaagtgat | 720 |
| ccgagcgacg atcaagagac gaaggacgag acaacgcttc agcgcgcgaa gagagcgagc | 780 |
| gaggaccctc ctggtcgaga ggctatccag tcgccaaccg gtacccatcc agtttgcagg | 840 |
| gttgaaacac agctgagagg atcagcgagt ggtagcgcaa actcctaagg cgctgaacgt | 900 |
| caaggacagc gagcgtgagc gtgtggaagc gacttgcgaa ggccaaactc gtgtcgcgct | 960 |
| ggccaaccgc cgtgccgctt tgacgcgctt ctgcgccctc cgcctattca gagagtatgc | 1020 |
| ttcgtcacgg cgtgggcgcc aacatcggcg caggagctgg cgggacggga agaaagccgc | 1080 |
| aaccgcggtc ctcgaccttc aacgtccggg gaggcccgtc cacgactccc agacgtctct | 1140 |
| gcttgttgtt ctacgtcgtc gcggcgttgt gcagagtcca gcgcgcgccc gtcgtcgact | 1200 |
| tctgacaagc gataaattcc gagaccagcg ggagaaggcg gaacgagagg aggaggcgag | 1260 |
| ctggcgtcct tgcgaccctcg ttgagcagtt caagcgagca gattgagcag cagtgcgtcg | 1320 |
| agtgagccaa ctcacgttct catatcggtc cctgagcgat atcgatgagg cgaaggacga | 1380 |
| cgacgagcga actgatctcg cgctctccct cttcccttc actctttcca ctcagaaaca | 1440 |
| acacgtgcgt cttctctgaa cgctatcaga caatccagga ccatcgctga ccgcgcgctc | 1500 |

```
actcgtcgcc tgacttcatc gcccaaccaa cccgctcgtc accgactgga tctctcccctc    1560 ccctcacacc acctgttgcg ctgcgatact cctctcacag ccatgg                    1606
```

<210> SEQ ID NO 7
<211> LENGTH: 1408
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1403)..(1408)
<223> OTHER INFORMATION: BamHI cloning site

<400> SEQUENCE: 7

```
actagtcggc gaagaggagg ggtgttagga gggagagctg tgcgaggggg agaggtcagt      60
ccgagcacga tacgcgagca ggccaagcgg cttcatgttc actccaagct cgatgcggtc    120
gagaagtacg agctccttga cgagtgaaag ggagagaaga gagactcacc aaccccggcg    180
cgaccttcac gaaccgcaac ttcccctcac acgcctcact acacgccctc tcaaacacct    240
cgagcgtcgc gtagtgcgag agcttgaaga ataggtaggc gaggaaggag gaggcgaaga    300
gggcggccat ctagcgaaca agttgggtta gctgggtggg ggaaagggaa gaggggagga    360 agaggggag ggtaccatga tccagcctat gtcgacttgc agttggaggg gcatcctgtg     420
cgcgtactgg cgtcagcggc ggacgacaag gcaggtagac gagagagggg gccggggaac    480
gcactcgcag ttgcgcacgt ccgagaggaa catgtacgag tagccggccc acatgacgct    540
cagcagcgcc gcaagcgtgt agtggaagat gagcctgccc attggcagtc agcgccgacg    600
cggacaaact ctgggtgaag agaaaggaga gaacgcacca cttctcctcc ttcagcactc    660
ccctcgccca gaccgccccc aacacaatac agacgagatc gatagttgcc ccagtcacag    720
cgagcgcgag ttggctgtag acgaggtgtt tgagccgtct gtgggcggga gaggtgcgga    780
tgcgctggat ctgcgcgggg gagagttttg ggacgaagtt ggggtcgtcg gccatggtga    840
gcccgtcgta gtagctgtct gagcgagcct agtagtgcgc tggacgagca gagcccagag    900
tcgagacgag cgtgagcagg agacgaggtt cggagtgtcc gcggagggcg acgagacgac    960
gagcgagctt gggagaagcg cgagcatgtc cagcagcgta gtctcgaggc cgccagcagt   1020
agtagagcac agcaatgagg caggaaggag cgcaagggag ggaaagagcg cgacgaaggg   1080
tcgaggtgat gaagtccaag gacaggggga ccaccctcgc ccgcttctcc ctcgctctcc   1140
ccacgaagtg accacttgta aggctggtaa ttcattccat acagtctaca tacacttgca   1200
gccatccgct tcccctgcga tgccagtttc ggtcaccgtg ggactccgat gcgatgatgc   1260
ggccgagttg gcttcctcga cccgctctca cacgctcata ccagcctctc ccagcctgct   1320
accgctctct ggctctgcca aacacccact cgagcacacc cacccaacca gcgaactcgc   1380
ccagcctttg aaccgcaatg gcggatcc                                      1408
```

<210> SEQ ID NO 8
<211> LENGTH: 1480
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: SpeI cloning site

```
<220> FEATURE:
<221> NAME/KEY: misc_feature
<222> LOCATION: (1475)..(1480)
<223> OTHER INFORMATION: NcoI cloning site

<400> SEQUENCE: 8
actagtcgtg cagaaggaac ccgaggaggt cagtgcgcgg tcgagagagg aaaaggagag      60
agagacgcac cgagcgaggc attgcgcgtg ccagcgctca gcctgtacct cgcgactgct    120
gatgaaagcg tcgtcgccgc ccgacatgac cgccgcctcg ctcgactggt cgccgacgac    180
gtcgacgccg gaaggaggtg cgccccagcc gcaggcggcg cgcctcaggc tcacgtcgac    240
gtgccggacg ttcgacgctc gccacgggtc gtgctcgagg gctttgacga cgagctcgtc    300
gcgctcggcg ctgccgcacc cattggcgaa cgtgacgtcc tggccgagca cctcctgcgc    360
gatggcgcgc cacaggcggc agacggacgc gacctggcgg taggcgcacg tgcgacaggt    420
gaccgtgagg tgcgcaaact ggccgtggac gaggagaggc tcagagatga gcgaggtcgt    480
gagggcgtgg cggatgacct tgaggaggag ctcgtgcggc acggcagaga gggtcggcat    540
gatggtgtgc ggcgcggtcg gcagtctcga gagagatgtg tagaggaaga acgatgtcgc    600
cagatcggtc gagcaggagc cggtgcgagg cggctcgagg accgtcgcgg tcgaggaccg    660
gtcacggctg gacgatcgag gagacgcgcc cccgtcgagc gcagcggcca gacgcaagcg    720
agcacctttg aggctgtact ccaaaacccg gagcgccggc tcgggagccg tgtcctcgca    780
ggatcctcgg tcgacagcgc cgagtcggag agggccagcc gacctcgggc cgcccgacgc    840
ccggccgcag ctcctccggt ccgacctgca gctcatccca gcagatcgac tttgagagcg    900
aagcccccag gaagctgcct gagcgacctc gaggcttggg aaggtcgccg agccacggct    960
gggagagcga gctccctcac agtcgagacc ggctccaagt cgaatcgcac actcgtagct   1020
gcaccgcaaa agtgtgtgca gagctggagc gagcgaccgc gcgaggcgcg agggtcgcga   1080
gaaagcgggc gagcggtgcg agtgcgcccg agacgccgag agaggcgcg agggcgagcg    1140 ggcctcgcga gccctctgga gcgtgcagag gcggcgggga ggagcagagt gagggaggga   1200
agaccctcca gagctggcag gagccaacgg agcgcggaaa tcagtgagat cgatgcggtt   1260
ctcgagacga ttcgaccgcc ctcgtcgtca acgtcgcgcc ctcgtccctc tcctcttccc   1320
accacctctc cggtacctct acacgagtgc gttctgtccc gagatctgat ctcgacgccg   1380
cacggcactg actgaccgcc cacctcgtct ccctcgcccg tcccacactc tcccttccga   1440
cctcccacct cctcgctcaa cccctctcgc ctcgccatgg                         1480

<210> SEQ ID NO 9
<211> LENGTH: 1532
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (1527)..(1532)
<223> OTHER INFORMATION: NcoI cloning site

<400> SEQUENCE: 9
actagtcggg aggattgatg atcgggttgc ggtacaaggc gaggccgagg acgagctgga     60
gggcgccgag gacgagggtc gagatgccga gctgcgaggg gacgaggccg ccaatcgagg   120
tcgtgtcaga cggccgtacc gagtgatctc atagcgggtc cgccgacgca gaaagacgaa   180
```

```
gagaaactca cgacgagggg gctcagcttg acaaagttga gctttgtcgt gcagccagac        240
gagctgcgat aggagcgagg gtcagtgcgc ccgctctcgg atgaatgcgc agtcgaggag        300 ggacagggc gcaccaggtg acgatgaaca tgtcgaggac gccgtactgc agcatcttgc         360
ggaagaggta gaaatgccac gccgaagcga aggtgacggc aaactgcgag agggacgagg        420
tcagtgcgag ggtccgcaac agggagaggg cactcgtcac ggaccatcat ccagcccagg       480
tcgatctgta gctgatcagg gaagctgtgc cgggtgcgag agaggtcaat gtcgaagctt        540
ggcagctcgt cgaggaagaa gaggacggcg agggacgcac gccatgaact tgatgtgacg       600
ctcgaagacg accgagtagc cgagccacat cattgtgagg acgccggcgc agacgtagtg      660
gaagatgaac ctgagagggc aagaggtcag tctcgaaacg agggaggaag ccggctcgag       720
caggacgagg cgggcgcaac ggacgcacca tttctcggcg cgacgatat tgcgagccca        780 cacggccccg agcactagac aggtgatgtt ggcgaccgcg ccgccgacgg cgagagcgag       840
aacgctgtag acgaagtgct tgatgcgtcg gtggattggc gctcgtcgga tcctcgcgat      900
ctgggccttg gtgagcggtg gtggcgggcc aagcggtggg ccagcagctg tgctcatcgc      960
agcagcggtg cggcgcaaga gcgactgtgg agctcgaggg agaggagcgc ggcaggggaa      1020
agcgagaccg aggaggagcg agcgcggaca ggcgaggcgc accggacgtt ccggtgcggc     1080
tcgactggcg tgcgagacga gcaggccgtc gccggaagca gccgtgtccg gcggaaagag      1140
ccaggcgcgc gagcggggcg gagcagacag cggcggtccg agcgcgcggg gcaggttcga     1200
cgaaagtcgg gctcgggtca ggctcgcgcg agcgcatgag atgccgtcga gcgagcccat     1260
gtacagagtc gagcgagaga gcgaagtgcg tggaaggaga gtggtccaag agtggagcgc     1320
cgtggagatg agacagatga tggcgaacct cggccacagc ctctcggtcc tgccacagca     1380
gctctgtgag tctccctgac ccgccagccc gcgcttcaga actcacagac cacctacaca    1440
gactcgcgca ccagctcgaa ccgcgccaga ccaccgcctc gccgcctccc cacctcgact   1500
gcttccgaac ctcacaagct cgaccaccat gg                                        1532
```

<210> SEQ ID NO 10
<211> LENGTH: 1222
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1217)..(1222)
<223> OTHER INFORMATION: NcoI cloning site

<400> SEQUENCE: 10

```
ggtaccgcga ggggaagggc aggagagtcg ccggaacacc gggcaaggag acaaggacaa        60
agagcgagcg cgcacgcacc gtctggcggt cgggctgggt ggggcgggtc cgagtagcgc       120
tgaccgaaga gcgaggagga ggaaaagcga gcgcggcggg cgtgggaagg agggcaagga     180
gggcggcggc gacgccaaaa aaggccagat cgcggggca gtgatcgagt gccgtccgcg        240
agctcaacca gcgagcgctc tctcgcgcgc agcggtgcgc ttctttcgcc agccgatgcg       300
caccgttcag aagcacgtcg cccgcaccga gagcgcctcc tcgcgagcct gtgaccacct       360
cgtcgacccg cttcccgcgg cttttctcgc cggcctggac cgccgctatc agatcgtgcc      420
catgagacaa gcgactcgtc gaaggacga cgatctcgta gtactgggtc cctgcgcaac       480
gctcagccgt ccgtccccgt caaagtgctt cggcggaggg gaccgtgcgc gagacgccca     540
```

| | |
|---|---|
| agttggcctc ctcaagtcgg tagatccagc ttaacgctat caagggttgc atggtgtagt | 600 |
| tggtcatcac gtcagtttaa cattcagttc actgaaggtc ctcagttcaa acctgggtgc | 660 |
| gatcaccttt ttggctcggc ggcattgcgc ccttacaccc gcacgggtct acttcccttt | 720 |
| gcaagcgacc aagcgaagca tcctctcgct cgtaaagctg ccggcgagga ggtcagacgg | 780 |
| gttggcgggc cgtcgaaggt cggctcaccc tcaacgctgc cggctgacca cgccaggcga | 840 |
| gctatcattg cttttgaaagc ttcgaaaacg cccaggcatg cacagaaagc cgcccgcgag | 900 |
| aggctcaagt tggcgccgag ctgcggtcga gagacgacga cgacgtggga gctccctcgc | 960 |
| ctctcctcct ttctctccca ccccatcagc ccaagtgagt cgctcgctct tccgcaaggg | 1020 |
| tcagcgcacg cgttgctccg cgacagggca gcgcgtgcgc tcaccagggt cccccgttcg | 1080 |
| cccggcgagt tggcactgac gaggtgcctt gcccccctcc gctcccctcc cctttggcct | 1140 |
| cctctctcgc acgcacactc tctccctgca ccccttgcac cttcccgaca ctctcccccc | 1200 |
| ccttcccacc gtccgaccat gg | 1222 |

```
<210> SEQ ID NO 11
<211> LENGTH: 1507
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1522)..(1527)
<223> OTHER INFORMATION: NcoI cloning site

<400> SEQUENCE: 11
```

| | |
|---|---|
| ggtaccacta cctcgtcacg acccagggtg cgttcccctt ctcgccgcgt ccacagccac | 60 |
| gacgttgcga gtccctaacg cgtccgctcc cccgtgcagg tggtcctccg cacggcgcct | 120 |
| acacgcagac atcgtcgacg ccgtcgcacg acgcccactt tgccgtccag accctgtcgc | 180 |
| gcttcggcct cgcgtacctc ctcgcgtcgt ccaacacgct caaggacacg tggctgagcg | 240 |
| tgtgcgcgcc cgccggcgcc aagggccccg aacccgacgt cgacgacctc gagctcgaga | 300 |
| agcgcgagca ccgcgacaag tggctcctcg ggcgcatcat gggccagggc aagcaggact | 360 |
| cggcgctcgg ggacgcagtc gctgtcgtga gtcctctact ctcggccgtt ctcgagactt | 420 |
| ggggtgcgag attgaccttg cgctcccgcc tctcgcttgc agcaattcca caagcacttt | 480 |
| ccgcacctgc gctcggcgca cctcttcccc ggctttgtct ttacgtgcgt ccctctcgtt | 540 |
| cccccctctc tccacgtgcg ccaccagcct gactcgcccc tcgcctgccc cgtcccgcag | 600 |
| caacgccctc gcgtcgacct cgctcgtccc ctcgccgatc ctgtcgctgt acaacctcgt | 660 |
| cgggcccctc gcggcgcgca tcctgccctt tggcaacctg cccgagacgt acgccgacgt | 720 |
| gcccgtgtac gtcgcggcca acccggcagc gcgcagccaa gggctcgagt actgcaacga | 780 |
| gcgcatgaag ccgctcggga gcccggcgtg ggccgagggc gcgacgggcg caaaggtgtg | 840 |
| ggacgggctg agggccatga tcgaggagtg agctggtggg cggcgagcg aggagccgga | 900 |
| gaggaggggc ggaacgtgtt tgagaaggtc gcgctttgct cgtcggtcgc gggcgcagcc | 960 |
| gtggctgtag ccagtctcgc tttgcagtgt cactcttgta catagctgag caaggcctag | 1020 |
| cgtcgcgaga gagctgcgct gtggcgcctg gtcgaggccc gagagcgtcg cgctcagggg | 1080 |
| cgagctgctc gcggctcacc aaggggcctcg agcggtgcgc gctcgacagg ggaccgagag | 1140 |
| ctgcaggaga cagaccggag gaaaaagctc tggcgagcga ggagcggggc cacactgagt | 1200 |

| | |
|---|---|
| ctggggaagc gacggacgag gatgagcgca tccactcttg agtttcgccg aggcgcgagc | 1260 |
| tggcggtcga caaccgagca agctcctcct cttcctccac cacactcgcc cctagcacac | 1320 |
| gtgagtctcg ctccctcgcc actgtcgacc agcacacgct cgtccaccgc cctgtgcgcc | 1380 |
| ctgtgcggct tgcggtcgag cgaggccgcg ggtcgggtct ctgccacccg aggaaccatc | 1440 |
| gatgtcgctg acgcttcgct cctcgtcctc ctcctcctcc cacccgccgc agctacctac | 1500 |
| accatgg | 1507 |

<210> SEQ ID NO 12
<211> LENGTH: 1646
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (1641)..(1646)
<223> OTHER INFORMATION: NcoI cloning site

<400> SEQUENCE: 12

| | |
|---|---|
| ggcgcgcctg aagctgtaca tcgaggtgga cgacagcgcg ggcaaggatg cgccagcaat | 60 |
| cgtttgtggg tcgcttcttt cctcgcagca cgcttttgtc ggctccctga tcagcacaca | 120 |
| agctaactaa cgctctggtt tcgctggcag tcatgcacgg ccttggctcg tcaacctcgt | 180 |
| tctgggaagc gcccttctcc cgctcaaacc tgtcctcccg cttccgcctc atccgctacg | 240 |
| acttcgacgg ccacggtctc tcgcccgtct cgtccctcga cgcagcagat gacggcgcca | 300 |
| tgatcccgct cgacgacctc gtcggggact tggcggctgt gatcgagtgg gctggggtgg | 360 |
| agaaggttgc gggagttgtt ggacactcga tgagcgggct ggtggcgagc acatttgcgg | 420 |
| ccaagtaccc gcagaagctc gacaagctcg gtgagtcgca ttgaaccttc ctccgccgtc | 480 |
| tcttctccgc tgacgattcg tcgacttggc cctgcttctc gcgcagtcct cctcggcgca | 540 |
| atgcgctctc tgaaccctac cgtccaaagc aacatgctca agcgagccga tacagtcctc | 600 |
| gaatccggcc tctcagcaat cgtcgcacaa gtcgtctccg ccgctttgtc cgacaagtca | 660 |
| aagcaggact cgcccctctc ggcagcgatg gtgcgaacgc tcgtgcttgg aacggacccg | 720 |
| agagggtacg cggcggcgtg tagggcgctt gcgggtgcga aggacccgga ttactcgagc | 780 |
| atcaaggccg agacgttggg tgcgttcgct tgttctcctt cctctgcttt tctcccagca | 840 |
| actgacgcaa gcgtctgcaa cacagtcgtc gcaggcgagt ttgactacct ctcgaacaag | 900 |
| gagacgaccg acgcgctggt caacgacatc ccgggcgcgg agaaggtcca gatggacagt | 960 |
| gtcggccact ggcacgccgt cgaggacccc gttggactcg ccaagatcct cgatgggttc | 1020 |
| ttcttgcagg ggaaatgagg ttgggaaggg gggatagact ggggagaacg gcaggtgcgt | 1080 |
| acgcagcgga cgtcggtcgg gaggactttt tcggggagga tattcgctga ctgactccga | 1140 |
| cgtcgctttc ctccttgcag tatcttcaga agggatggga ggaggcgaac tgcaagggta | 1200 |
| atgaacgaga caacgccgag ggaggaagcg ccggaactct cggggggcgaa gaaggagtgg | 1260 |
| tgtcttcgcc agcgaacagc ttccggggtg ggttggacag cgccagtaga attccagcgt | 1320 |
| cgcaacagag ctctagtcga ccgcgatcac ccacaaggac gagagcgggt cgcgccttgt | 1380 |
| ccgcttcccc atcctcgtcc tgctcttgct ctcttcccta ccacactctc ccgcttgcgg | 1440 |
| gctctctttc tcgcttggcg ctcctgctac cgctactcta gactctccta gtctccctgc | 1500 |
| acaaccatcc ctatccctc cgcctctctc gcacacccc cacagcttcg ttccccaact | 1560 | tcacttccga tgccgtgcgt cgcctcccct tcgcctggcg ggcccgcgcc tgcttccgag    1620 gacaactact gattgtggga ccatgg    1646

<210> SEQ ID NO 13
<211> LENGTH: 28
<212> TYPE: DNA
<213> ORGANISM: Artificial Sequence
<220> FEATURE:
<223> OTHER INFORMATION: PCR primer

<400> SEQUENCE: 13
aaaggtaccg tgcgagaaga agcgaggc                                         28

<210> SEQ ID NO 14
<211> LENGTH: 34
<212> TYPE: DNA
<213> ORGANISM: Artificial Sequence
<220> FEATURE:
<223> OTHER INFORMATION: PCR primer

<400> SEQUENCE: 14
aaaccatggt tcccccccag tacacagtac agta                                  34

<210> SEQ ID NO 15
<211> LENGTH: 29
<212> TYPE: DNA
<213> ORGANISM: Artificial Sequence
<220> FEATURE:
<223> OTHER INFORMATION: PCR primer

<400> SEQUENCE: 15
aaaggtaccc atgctgctgc tgcccctca                                        29

<210> SEQ ID NO 16
<211> LENGTH: 31
<212> TYPE: DNA
<213> ORGANISM: Artificial Sequence
<220> FEATURE:
<223> OTHER INFORMATION: PCR primer

<400> SEQUENCE: 16
ataccatggt ggatgaagtg agattcgagt g                                     31

<210> SEQ ID NO 17
<211> LENGTH: 29
<212> TYPE: DNA
<213> ORGANISM: Artificial Sequence
<220> FEATURE:
<223> OTHER INFORMATION: PCR primer

<400> SEQUENCE: 17
aaaggtaccc aaagggagag gagcgggcg                                        29

<210> SEQ ID NO 18
<211> LENGTH: 33
<212> TYPE: DNA
<213> ORGANISM: Artificial Sequence
<220> FEATURE:
<223> OTHER INFORMATION: PCR primer

<400> SEQUENCE: 18
aaaccatggt gacctacgcc tacacaaggg tgc                                   33

<210> SEQ ID NO 19
<211> LENGTH: 28
<212> TYPE: DNA
<213> ORGANISM: Artificial Sequence
<220> FEATURE:
<223> OTHER INFORMATION: PCR primer

<400> SEQUENCE: 19
aaaggtacct gagcgggcga gccgcgag                                      28

<210> SEQ ID NO 20
<211> LENGTH: 33
<212> TYPE: DNA
<213> ORGANISM: Artificial Sequence
<220> FEATURE:
<223> OTHER INFORMATION: PCR primer

<400> SEQUENCE: 20
aaatcatgac tgaacaaagt tttcctgcgg cgc                                33

<210> SEQ ID NO 21
<211> LENGTH: 31
<212> TYPE: DNA
<213> ORGANISM: Artificial Sequence
<220> FEATURE:
<223> OTHER INFORMATION: PCR primer

<400> SEQUENCE: 21
aaaggtaccg ctcatcatcg agcgagggca g                                  31

<210> SEQ ID NO 22
<211> LENGTH: 32
<212> TYPE: DNA
<213> ORGANISM: Artificial Sequence
<220> FEATURE:
<223> OTHER INFORMATION: PCR primer

<400> SEQUENCE: 22
aaaccatggc ggcgggtgat tcttcttggt tc                                 32

<210> SEQ ID NO 23
<211> LENGTH: 28
<212> TYPE: DNA
<213> ORGANISM: Artificial Sequence
<220> FEATURE:
<223> OTHER INFORMATION: PCR primer

<400> SEQUENCE: 23
gactagtcgc cagggaacgc agagaagg                                      28

<210> SEQ ID NO 24
<211> LENGTH: 29
<212> TYPE: DNA
<213> ORGANISM: Artificial Sequence
<220> FEATURE:
<223> OTHER INFORMATION: PCR primer

<400> SEQUENCE: 24
aaaccatggc tgtgagagga gtatcgcag                                     29

<210> SEQ ID NO 25
<211> LENGTH: 30
<212> TYPE: DNA
<213> ORGANISM: Artificial Sequence
<220> FEATURE:
<223> OTHER INFORMATION: PCR primer

<400> SEQUENCE: 25
gactagtcgg cgaagaggag gggtgttagg         30

<210> SEQ ID NO 26
<211> LENGTH: 34
<212> TYPE: DNA
<213> ORGANISM: Artificial Sequence
<220> FEATURE:
<223> OTHER INFORMATION: PCR primer

<400> SEQUENCE: 26
aaaggatccg ccattgcggt tcaaaggctg ggcg         34

<210> SEQ ID NO 27
<211> LENGTH: 29
<212> TYPE: DNA
<213> ORGANISM: Artificial Sequence
<220> FEATURE:
<223> OTHER INFORMATION: PCR primer

<400> SEQUENCE: 27
gactagtcgt gcagaaggaa cccgaggag         29

<210> SEQ ID NO 28
<211> LENGTH: 28
<212> TYPE: DNA
<213> ORGANISM: Artificial Sequence
<220> FEATURE:
<223> OTHER INFORMATION: PCR primer

<400> SEQUENCE: 28
aaaccatggc gaggcgagag gggttgag         28

<210> SEQ ID NO 29
<211> LENGTH: 31
<212> TYPE: DNA
<213> ORGANISM: Artificial Sequence
<220> FEATURE:
<223> OTHER INFORMATION: PCR primer

<400> SEQUENCE: 29
gactagtcgg gaggattgat gatcgggttg c         31

<210> SEQ ID NO 30
<211> LENGTH: 26
<212> TYPE: DNA
<213> ORGANISM: Artificial Sequence
<220> FEATURE:
<223> OTHER INFORMATION: PCR primer

<400> SEQUENCE: 30
aaaccatggt ggtcgagctt gtgagg         26

<210> SEQ ID NO 31
<211> LENGTH: 33
<212> TYPE: DNA
<213> ORGANISM: Artificial Sequence
<220> FEATURE:
<223> OTHER INFORMATION: PCR primer

<400> SEQUENCE: 31
aaaggtaccg cgaggggaag ggcaggagag tcg         33

<210> SEQ ID NO 32
<211> LENGTH: 32
<212> TYPE: DNA
<213> ORGANISM: Artificial Sequence
<220> FEATURE:
<223> OTHER INFORMATION: PCR primer

<400> SEQUENCE: 32
aaaccatggt cggacggtgg aagggggggg ga                                  32

<210> SEQ ID NO 33
<211> LENGTH: 33
<212> TYPE: DNA
<213> ORGANISM: Artificial Sequence
<220> FEATURE:
<223> OTHER INFORMATION: PCR primer

<400> SEQUENCE: 33
aaaggtacca ctacctcgtc acgacccagg gtg                                 33

<210> SEQ ID NO 34
<211> LENGTH: 29
<212> TYPE: DNA
<213> ORGANISM: Artificial Sequence
<220> FEATURE:
<223> OTHER INFORMATION: PCR primer

<400> SEQUENCE: 34
aaaccatggt gtaggtagct gcggcgggt                                      29

<210> SEQ ID NO 35
<211> LENGTH: 34
<212> TYPE: DNA
<213> ORGANISM: Artificial Sequence
<220> FEATURE:
<223> OTHER INFORMATION: PCR primer

<400> SEQUENCE: 35
aaaggcgcgc ctgaagctgt acatcgaggt ggac                                34

<210> SEQ ID NO 36
<211> LENGTH: 37
<212> TYPE: DNA
<213> ORGANISM: Artificial Sequence
<220> FEATURE:
<223> OTHER INFORMATION: PCR primer

<400> SEQUENCE: 36
aaaccatggt cccacaatca gtagttgtcc tcggaag                             37

<210> SEQ ID NO 37
<211> LENGTH: 672
<212> TYPE: DNA
<213> ORGANISM: Ustilago maydis
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (667)..(672)
<223> OTHER INFORMATION: NcoI cloning site

<400> SEQUENCE: 37
ggtaccggcg cgctagtcct taaaactgaa ggcgggaaac gacaatctga tccaagctca    60
agctaagctc tagtgattag atcttgctga taggcaggtt tgcttggaga atggggggaa   120

```
aagactgacc gaagaaacag cgagatctag aagtgataag cggaaagaat ctgacttgct      180
gtgatcagca gccaattttt ttttcgtttt ttttttttca ctccacatcg tcgtgcgtgc      240
acggtctgca tgtgtaaatt gtattcatcg aaagccacag ttgaatacat cagcccgatg      300
tggatttcga aaccaatta  atcttggaat tcacgcgctc agatcagtcc atagagtcga      360
cttcggctgt ttccaagagc ttcttctctg cgaggtggtt gcccgtgttt ctcgctggga      420
aaaaaggatc gattattatt cgcttctacc tcgctcgcac ccttggcctg ctgaaggaaa      480
cagcgccgag actcggtcac ggttgctggg ctccgtgttg atgctgggac ggcgcaaagt      540
ggggcccgcg cactcttcga gccaaggacc tcactcttca agaacaagcg ctgtcgccat      600
cgtcttcttc tttctgctcc accatcgaat ctttcttct  cgtttcgaaa ccaaaacact      660
cttccaccat gg                                                          672
```

```
<210> SEQ ID NO 38
<211> LENGTH: 1450
<212> TYPE: DNA
<213> ORGANISM: Rhodosporidium toruloides
<220> FEATURE:
<221> NAME/KEY: misc_feature
<222> LOCATION: (1)..(6)
<223> OTHER INFORMATION: KpnI cloning site
<220> FEATURE:
<221> NAME/KEY: misc_feature
<222> LOCATION: (1445)..(1450)
<223> OTHER INFORMATION: NcoI cloning site

<400> SEQUENCE: 38
```

```
ggtaccggcg cgctagtctg cagaactacg ccctctcaca cccaacttcc gactcgaccg       60
gcggtacgag cacgacctac ttctactgcc tgccatcgac atccgggcgg gtcgctgcct      120
accctgtgcg ttctgcgccc tccctcgtct cgggaggcag tgtctgacag aagctttgcg      180
cgcagtaccc cgtcaagatg caactctacg caacgttcgg cacagaagtc gccaagctcc      240
gcgcatcgcc gcctcaagct ctcgcgctgc ccgacggtgt cgtctattac gaggcggaga      300
agctcgagtt gccggctttg ccagcggcgg tcaaggttga ggtggagacg agaaggcgg       360 gagtagcggg ggaggacaat gaggcgaagg gtgagatggt gctggtggag actcttacgg      420
tggagcagga ggagattgaa ttgggctcgg gagtcgtgca gattgaggag tcgttgctcg      480
tcaagctgga ggtcagcggc tgatccttcc gttcgttgca aggatcgtct gcatgtttcg      540
cttctctcaa tgacacaacc tggagagcgc tcccgtcagc gagaatcgag acattccgc      600 agctcgtgag caagcggagg tgcgaggctc cctcgaaagc tgcgcctctt cagacggctt      660
gttctctcct gctctggtgg gctggcctga catgtaatgt gctccgccgc aagtccgtcg      720
tcggtctcaa ttcgacgttg aaagggcata gcgcaaggaa gaaccctctg cggacatgca      780
gaattactgg ctcgcctgct ccttcgtcta ctggaataag tcctgtctcg ttaaagcccc      840
aacgtcgttt ttcgacgttt gtaaggcgca agaggtgcta tgggctacgc aggaagctga      900
gaggacatag aagtcggggg aggaacggcg cagagcggca gttgcggaag catgaggaaa      960
gcgagacggt ccagcatctg cagcgccaat ccgcaatctc ctggttgagc ctgcaccgga     1020
agcgtcggaa cagtatgcgc agagtcgaac gcaagtaaga aagacgcacc ctcacactcg     1080
cttacttcga gccatacaac ggatcaaagc tgcgcgtatc tcggcttgta agggccggaa     1140 agcaaccctcg gagatggaca cgtcacatca ccaacttatc gatctcggcc gtcgacgtcg     1200
cagagagggc gagagaagcg gtgaaggagg gaaacaaccc ctcgagagca tgatccgacc     1260
gaatctgcag cgcaggaagc cgttacaagc ccgcctcgag cgcaggtcgg gtccagccgg     1320
```

| | | |
|---|---|---|
| gggacgaaac gcgcgaggct gattcgtgag cgaaggaagc cgcatcgaca agttcgctcc | 1380 | |
| cctttgccct ctttcccatc acccgttctc gccttacccg ctcagaacaa caccagatca | 1440 | |
| ctcaccatgg | 1450 | |

<210> SEQ ID NO 39
<211> LENGTH: 963
<212> TYPE: DNA
<213> ORGANISM: Rhodotorula graminis strain WP1
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (958)..(963)
<223> OTHER INFORMATION: NcoI cloning site

<400> SEQUENCE: 39

| | |
|---|---|
| ggcgcgccta cgtctacgtc aagggcaatg ccgacgtgac caaggccatc ggccaggacc | 60 |
| tcgccttctt ctcggtccct gtcgagctcg gcgtgcgtcc cgccgctctc tctctctctt | 120 |
| tctctcggcc gcgcctcacg tgatccacga cgtcgtactg acccttgcga atgtgcgcgc | 180 |
| ccgcagccca acggcgtcga gaaggtgcac ccgctcggcg acctgacggc gttcgagaag | 240 |
| gagctcctcg aggcgtgcct cggcgagctg cccgggtcca tctccaaggg cgagtcgttc | 300 |
| atccagggct ccaagctctg actcgccggc gcatcgacgg gcgcgagcca caaggcgagg | 360 |
| atgtgagagg aggcgtttcc tccaccttgg accccatctg ccgcctccct ttctctctct | 420 |
| ttctttccct tcctctctct ctctctctct ctcgttctcc tccttctggg cctctcggac | 480 |
| ctcttcctcg ccgtcgactc gtgaaaatgc agtgcgcgtt tctgtacctt gtcctgcgag | 540 |
| agagatctgt ttctgcgagg gtgagtcgtt gccttggccg tggcacgcct cgccgcagcg | 600 |
| agagagaaga ggccacggtc caggacgacg acgacgagga ggaagcgcaa aaggcgagac | 660 |
| accgagtgcc atcgattccc cgctcgaacc tgctcacggc tgtcgaaggc ggtgcgccac | 720 |
| ggtgcttgcg ggagcgaaag caagctggcg tcgtcctctt gaactggttc gagtccgtga | 780 |
| gggcggcgac gagaactcag gcgaggtgct cgcgtcggaa caagccgggc ttgtggtcga | 840 |
| gggagcgaga gcgaggcagc gccgtcgtcg ccgaggcaag agcggcatcg acaagttggc | 900 |
| ccgtcgcctc tcgctcccctc ttctcctcct cccaccacca cctttctcca gctcgaacca | 960 |
| tgg | 963 |

<210> SEQ ID NO 40
<211> LENGTH: 2148
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (2143)..(2148)
<223> OTHER INFORMATION: NcoI cloning site

<400> SEQUENCE: 40

| | |
|---|---|
| ggcgcgccac catctcctcg tcgcttcttc cctctccttc ggcgcccaca ccgcttcgca | 60 |
| gggctcacgg actgctcaca tcgtttgtgt gcgtcgctgt gcatgtccac gcaccactcc | 120 |
| cagccccac gagcgcctca aaagacgcgg acgcagacgc ccgccgaacg acggcacgcc | 180 |
| cctcttctca ctagcgcgac gaaccagctg cgacgattcg tgcgcttatg ttagccggac | 240 |

| | | | | |
|---|---|---|---|---|
| ttctggcttg | ctttgcgctg | ctgcgtccgt | cttgtggtgc | ggatcggctc | gatgggggtt | 300 |
| tgctcgtttg | ctgggagacg | gtcgcctctc | cctcctcctc | ttcactcctc | gttagctttc | 360 |
| tacgctcatt | ggttctgcga | accatctaca | tcacgctcgc | tcgtcatgct | cgtactacga | 420 |
| tcaacacccc | tgctcgtcgt | gctttcccte | ctctccgtcc | tctcggccgc | gtccagcgac | 480 |
| ttgcccagcc | aacttccccc | gcacgccggt | gagtctccca | cacttccttg | cgaccccaac | 540 |
| ccagcatctg | acatccgcat | cacgcagccc | tcccgccttc | ccactcctcc | ctcttcaccg | 600 |
| actcctcctc | ctcctcccct | gattcctcgt | ccctcaaagc | cccgcagcct | cttcccttca | 660 |
| aaatcaagcg | ccccgctcg | ctcgaacaag | tgcagcagaa | cctcgggaag | aggctggcga | 720 |
| agcgcggcga | ggaggggagt | aagacggaga | gggtgccgtt | tggtcagagg | agtgcgacgg | 780 |
| cggcgagtgc | gggtggacaa | ggtgagcgg | ggacggggag | ggcgacgcag | cgcgttacgg | 840 |
| gcggaggaag | cagaggtgca | ggaggaggcg | gagggagtgt | cgcggctgct | cagcctgtcc | 900 |
| cttcgactac | ccagacggtc | gagacaggct | ctaagatcgt | ctcgactggt | cttctgaccg | 960 |
| tagcgtcgcc | gtcgacggca | gatggaggag | gcggacggg | cacccaggtc | gagacggcct | 1020 |
| cctcaggggt | attgatcacc | agcacggcgg | gagcggcgag | ttcagcggcg | gcgtcggacg | 1080 |
| tcgctagcgc | acaggcagcg | gaggcgacgt | cgagtacgac | catgatcagc | ggaggagcgg | 1140 |
| cggctggcgg | gagtttaagc | aggatgctgg | cgggaggagt | tgcgggtgca | gccctgatcc | 1200 |
| tcctcgtgcg | gtgagcaggc | gaagcgagga | gctcatgtag | atacagcata | gacagtatat | 1260 |
| atcgccagga | tagcttgcaa | cagccgccgg | tcggtttatt | ccattgtcct | cgaccccatg | 1320 |
| cgaaggcgag | ctctgctcgt | cagctggcca | agctggccag | cagacgagcg | ttggggtggc | 1380 |
| ggaacgccaa | cggcatggag | taaagcagcc | gtgaggatga | cggaggagct | cggcgaggt | 1440 |
| gatgggatt | ctagcaggaa | cagcagagcg | gcgaggagga | gaggaaccgg | aagcacagtc | 1500 |
| tcgtggccgc | ttgttgcaga | tcccagtgtc | gctagagtgc | tcgtcgtcat | cagagcgagt | 1560 |
| gaacaaagcg | atgcccctgaa | gaacgatgag | cgaatgagtc | gaagcggcgt | ctaccggtga | 1620 |
| actcggggtg | tggcaaatga | gcgagacgag | gagtgcccgc | cagagttgcc | acgtcgaccc | 1680 |
| cacgtcggaa | tcgacgttga | tagagtgaac | gaagccattg | cagaccccag | aaggtggcca | 1740 |
| tgttgtggaa | gcgagggcag | gagcgagggg | agaaggcgag | gaggaggagg | ggctggggaa | 1800 |
| gcccgtccgg | gaatggcgca | gctgggtgcc | ggggatgtgc | gcgagtggcg | gaggagtcga | 1860 |
| gcgtgagagt | tctggaacac | ggggcgcgca | caagggtcga | gggccgtgac | gagttcgccg | 1920 |
| ggcggtggtc | gggctgaggg | cgagcgcgcg | ttggggacga | cgacgcccga | cgccctcgct | 1980 |
| cttcgtcctc | accgcttccc | ggagaacttt | gctgtactct | gcttctccct | tcacactctc | 2040 |
| acacccactc | acacacccctt | ccatccacac | acaagctatc | cgcacacctc | tcacacccga | 2100 |
| ccccagctcg | ccccatcctc | ttcgcacccg | gctcatcgaa | aaccatgg | | 2148 |

```
<210> SEQ ID NO 41
<211> LENGTH: 1009
<212> TYPE: DNA
<213> ORGANISM: Sporobolomyces roseus
<220> FEATURE:
<221> NAME/KEY: misc_feature
<222> LOCATION: (1)..(6)
<223> OTHER INFORMATION: AscI cloning site
<220> FEATURE:
<221> NAME/KEY: misc_feature
<222> LOCATION: (1004)..(1009)
<223> OTHER INFORMATION: NcoI cloning site
```

```
<400> SEQUENCE: 41
ggcgcgccga agttatacct cagaggtctc aaaaacgaaa aagtcatgca agaatctcct      60
ttgacgtgag ggttatttct cttcctctag tagtctacga gaatcgcaaa gatcggaaaa     120
ctgatgcatc tttgtgttca cgggttagcg atttgatctt ttcgattccc aaaatcgtat     180
cgttcctgtc gcagggaact acgctcaaag ccggcactct gatcatcacg ggagtgagtt     240
ttgagctctc cctctatgag agtgcaaggt tcgtcgctga tggtgtaatc cgctcatgcc     300
ttcccctcta ccttctcctt tgtccattct ctctactacg gttgtcacat cttccttctc     360
cgacagaccc cgcacggaat tggagcgtac tcgaatcctc cggaattctt caaggacgga     420
gacgtcttca gggtcgagat ctcgggaggc atcgggagtt tggtcaacaa gatcgaatat     480
gaaaagtaga taatccgtta ctcaggtcaa tggtatggct tcgaagatgc tggaatcagc     540
cggaaagcaa agctggagag aaaaatcgag attgcgaaac gtgcgatgtc atttcgtttc     600
gagctcgcaa ccatctcgta tccctctgag ctacatacaa acgtcactac ggcctcggag     660
tgactccctg cgagcggatt gaaggagatc acggtcgaat cagctagacc ttcgcaacgt     720
tttcgcgctc gcacgttctt atcgatctac tgagattgac tcgaaaaagt cttctctcac     780
ggtcgattga actttgaatg aactctcagg ttgcgcgaga gccaatacga gccgaccaga     840
ggcaattcgg agcttcccgg aacgttccaa ggagagggat tttccgagag attacgattg     900
cgagatagaa aaaaggctag cttttcgattt cgagagagat tactttcaag ttcgctgctt     960
ccaactcttg ctccaacccc ctccactcct tctctacaaa acaccatgg              1009

<210> SEQ ID NO 42
<211> LENGTH: 529
<212> TYPE: DNA
<213> ORGANISM: Rhodotorula glutinis ATCC 204091
<220> FEATURE:
<221> NAME/KEY: misc_feature
<222> LOCATION: (1)..(6)
<223> OTHER INFORMATION: SpeI cloning site
<220> FEATURE:
<221> NAME/KEY: misc_feature
<222> LOCATION: (524)..(529)
<223> OTHER INFORMATION: NcoI cloning site

<400> SEQUENCE: 42
actagtcgcg gtcctcgacc ttcaacgtcc cgggaggccc gtccacgact cccagacgtc      60
tctgcttgtt gttctacgtc gtcgcggcgt tgtgcagagt ccagcgcgcg cccgtcgtcg     120
acttctgaca agcgataaat tccgagacca gcgggagaag gcggaacgag aggaggaggc     180
gagctggcgt ccttgcgacc tcgttgagca gttcaagcga gcagattgag cagcagtgcg     240
tcgagtgagc caactcacgt tctcatatcg gtccctgagc gatatcgatg aggcgaagga     300
cgacgacgag cgaactgatc tcgcgctctc cctcttcccc ttcactcttt ccactcagaa     360
acaacacgtg cgtcttctct gaacgctatc agacaatcca ggaccatcgc tgaccgcgcg     420
ctcactcgtc gcctgacttc atcgcccaac caacccgctc gtcaccgact ggatctctcc     480
ctcccctcac accacctgtt gcgctgcgat actcctctca cagccatgg                 529
```

POLYNUCLEOTIDE SEQUENCES FROM RHODOSPORIDIUM AND RHODOTORULA AND USE THEREOF

CROSS-REFERENCE TO RELATED APPLICATIONS

The present application is a 371 U.S. National Phase application of corresponding International Application No. PCT/SG2014/000114, filed 10 Mar. 2014, and is related to and claims priority to U.S. Provisional Patent Application Ser. No. 61/782,832, filed 14 Mar. 2013. Each application is incorporated herein by reference.

SEQUENCE SUBMISSION

The present application includes a Sequence Listing in electronic format. The Sequence Listing is entitled 2577230US2RevSequenceListing.txt, was created on 6 Feb. 2018 and is 40 kb in size. The information in the electronic format of the Sequence Listing is part of the present application and is incorporated herein by reference in its entirety.

BACKGROUND OF THE INVENTION

The present invention relates to the field of fungal biotechnology, more particularly to strong gene expression systems in species in the Pucciniomycotina and Ustilaginomycotina subphyla.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

The Pucciniomycotina is a subphylum of fungi in the phylum of Basidiomycota (Kirk et al., 2008). It holds many species that have important industrial applications. For example, a number of species in the *Rhodosporidium* and *Sporidiobolus* genera, such as *Rhodosporidium toruloides* (also known as *Rhodotorula gracilis*, *Rhodosporidium glutinis*, *Rhodotorula glutinis*, *Torula koishikawensis* and *Torula rubescens*) and *Sporobolomyces salmonicolor*, are oil-rich single-cell yeasts capable of high density fermentation (Hu et al., 2009; Meng et al., 2009). These species hold great potential as a host for the production of long chain hydrocarbons, such as triacylglycerol (TAG, or fat), fatty acid esters (biodiesel), fatty alcohols, alcohols, lactones, terpenoids and vitamins (Wu et al., 2010a; Wu et al., 2010b; Zhao et al., 2010a; Zhao et al., 2010b). In another example, species in Ustilaginomycotina subphylum, in particular, *Ustilago* and *Pseudozyma* genera, are known to produce glycolipids, which may function as a surfactant or fungicide (Hewald et al., 2005; Teichmann et al., 2010).

Promoters that are able to drive strong gene expression, either constitutively or inducibly, are critical for the development of biotechnological applications of a microorganism. WO 2012/169969, incorporated by reference herein in its entirety, describes several polynucleotide sequences derived from the upstream region of glyceraldehyde phosphate dehydrogenase gene (GPD1), translation initiation factor gene (TEF1), and putative stearoyl-CoA-delta 9-desaturase gene (FAD1) of selected fungal species that are able to function as a strong promoter of gene expression in Pucciniomycotina and Ustilaginomycotina subphyla. As repeated use of the identical or highly homologous promoter risks genome instability, epigenetic and genetic modification of chromatin resulted from repeat induced point mutation (RIP) or RNA silencing (Horns et al, 2012), an enlarged promoter pool is highly desirable for Pucciniomycotina and Ustilaginomycotina subphyla, wherein functionally verified promoters are scarce.

Promoters are DNA sequences located in the 5' region adjacent to the transcriptional start site. It houses a combination of cis-acting DNA elements that act to interact with transcription factors by activating or repressing transcription of RNA polymerase. To date, genome shotgun sequences have been published for *Rhodotorula glutinis* ATCC 204091 (GenBank Accession: GL989638.1), *Rhodosporidium toruloides* MTCC 457 (GenBank Accession: PRJNA112573), *Rhodosporidium toruloides* NP11 (GenBank: ALAU00000000.1) and draft genome sequences have been published for *Rhodotorula graminis* WP1 (http://genome.jgi-psf.org/Rhoba1_1/Rhoba1_1.home.html) and *Sporobolomyces roseus* (http://genome.jgi-psf.org/Sporo1/Sporo1/Sporo1.home.html). RNA-Seq, proteomic and genome shotgun data released for *Rhodosporidium toruloides* NP11 (Zhu, Z., et al, 2012) are not able to define the sequence of functional promoters because the activity of a promoter is influenced by several factors, such as the location of 5' and 3' ends, posttranscriptional silencing, influence of intron, etc. The activity of a promoter in a heterologous host species is even more unpredictable.

SUMMARY OF THE INVENTION

The present invention relates to the field of fungal biotechnology, more particularly to strong gene expression systems in species in the Pucciniomycotina and Ustilaginomycotina subphyla.

In a first aspect, the present invention provides polynucleotide sequences that function as strong promoters of gene expression in *Rhodosporidium*, *Rhodotorula*, *Sporobolomyces*, *Pseudozyma* and *Ustilago* genera. These polynucleotide sequences are sometimes referred to herein as polynucleotide promoter sequences. In one embodiment, the polynucleotide promoter sequences comprises the sequence set forth in any one of SEQ ID NOs:1, 2, 3, 4, 5, 6, 7, 8, 9, 10, or 11. In another embodiment, the polynucleotide promoter sequences comprises the promoter sequence of any one of SEQ ID NOs: 1, 2, 3, 4, 5, 6, 7, 8, 9, 10, or 11, i.e., the sequence without the cloning sites. Each of the polynucleotide promoter sequences contains at least one GAGGAG sequence motif, which functions to enhance gene expression in said fungal species. Each of polynucleotide sequences is effective in performing strong gene expression in *Rhodosporidium*, *Rhodotorula*, *Sporobolomyces*, *Pseudozyma* and *Ustilago* genera. In addition, operable fragments of these polynucleotide promoter sequences can be isolated using convention promoter screening assays and can be screened for efficient selection of transformed fungal cells using the techniques described herein. In one embodiment, an operable fragment, also termed a promoter portion herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs.

In a second aspect, the present invention provides a DNA construct comprising the polynucleotide promoter sequences described herein, an operably linked polypeptide encoding sequence and an operably linked RNA transcriptional terminator sequence. Any eukaryotic transcriptional terminator, well known to the skilled artisan, may be used. Such a DNA construct allows strong expression of the polypeptide in a fungal species in which the genome is biased in C and G. Of particular relevance are species selected from the Pucciniomycotina and Ustilaginomycotina subphyla. The species of particular relevance are those in the *Rhodosporidium, Rhodotorula, Sporobolomyces, Ustilago* and *Pseudozyma* genera, in which reside a number of species with great potential for the bioconversion of renewable resources into high-value products, such as triglyceride, biodiesel, fatty alcohol, vitamins, lactone, terpenoids and biosurfactants.

DETAILED DESCRIPTION OF THE INVENTION

Figure 1:
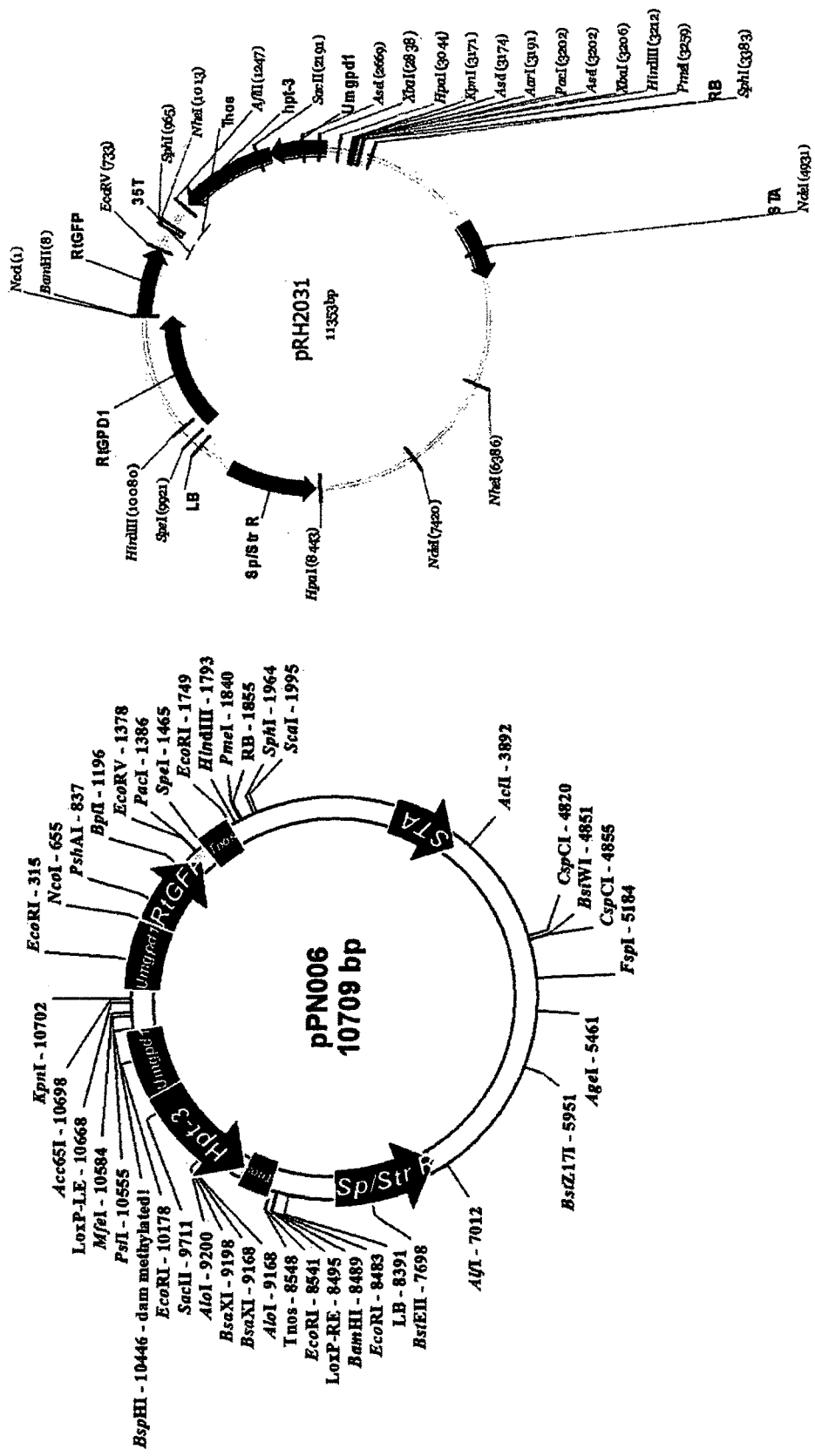
FIG. 1 shows cloning and transformation vectors for promoters. Both pPN007 and pRH2031 are based on pPZP200 and contain the Umgpd1::hpt-3 hygromycin selection marker. RtGFP is a codon optimized GFP gene optimized for GC-rich genome.

Unless defined otherwise, all technical and scientific terms used herein have the same meaning as is commonly understood by one of skill in the art to which the invention belongs.

The term "operably linked" or "operatively linked" is defined herein as a configuration in which a regulatory or control sequence is appropriately placed at a position relative to the nucleotide sequence of the nucleic acid construct such that the control sequence directs the expression of a polynucleotide of the present invention. Regulatory or control sequences may be positioned on the 5' side of the nucleotide sequence or on the 3' side of the nucleotide sequence as is well known in the art.

The term "strong expression" as used herein means expression of a marker protein or mRNA to a detectable level using detection methods known, for example, florescence for GFP, activity assay for GUS and lacZ genes.

The present invention relates to the field of fungal biotechnology, more particularly to strong gene expression systems in species in the Pucciniomycotina and Ustilaginomycotina subphyla.

In a first aspect, the present invention provides polynucleotide sequences that function as strong promoters of gene expression in *Rhodosporidium, Rhodotorula, Sporobolomyces, Pseudozyma* and *Ustilago* genera. These polynucleotide sequences are sometimes referred to herein as polynucleotide promoter sequences. In one embodiment, the polynucleotide promoter sequences comprises the sequence set forth in any one of SEQ ID NOs:1, 2, 3, 4, 5, 6, 7, 8, 9, 10, or 11. In another embodiment, the polynucleotide promoter sequences comprises the promoter sequence of any one of SEQ ID NOs: 1, 2, 3, 4, 5, 6, 7, 8, 9, 10, or 11, i.e., the sequence without the cloning sites. Each of the polynucleotide promoter sequences contains at least one GAGGAG sequence motif, which functions to enhance gene expression in said fungal species. Each of polynucleotide sequences is effective in performing strong gene expression in *Rhodosporidium, Rhodotorula, Sporobolomyces, Pseudozyma* and *Ustilago* genera. In addition, operable fragments of these polynucleotide promoter sequences can be isolated using convention promoter screening assays and can be screened for efficient selection of transformed fungal cells using the techniques described herein. In one embodiment, an operable fragment, also termed a promoter portion herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs.

In a second aspect, the present invention provides a DNA construct comprising the polynucleotide promoter sequences described herein, an operably linked polypeptide encoding sequence and an operably linked RNA transcriptional terminator sequence. Any eukaryotic transcriptional terminator, well known to the skilled artisan, may be used. Such a DNA construct allows strong expression of the polypeptide in a fungal species in which the genome is biased in C and G. Of particular relevance are species selected from the Pucciniomycotina and Ustilaginomycotina subphyla. The species of particular relevance are those in the *Rhodosporidium, Rhodotorula, Sporobolomyces, Ustilago* and *Pseudozyma* genera, in which reside a number of species with great potential for the bioconversion of renewable resources into high-value products, such as triglyceride, biodiesel, fatty alcohol, vitamins, lactone, terpenoids and biosurfactants.

Nucleic acid hybridization, a technique well known to those of skill in the art of DNA manipulation, can be used to identify other suitable polynucleotides. In accordance with the invention other suitable promoters for use may be obtained by the identification of polynucleotides that selectively hybridize to the promoters described above by hybridization under low stringency conditions, moderate stringency conditions, or high stringency conditions. Selectively hybridizing sequences typically have at least 50% sequence identity, preferably at least 70%, 80% or 90% sequence identity, and most preferably 95%, 98% or 99% sequence identity with each other.

Database searches and homology searches of genome and nucleotide databases identify similar DNA or RNA molecules based on the alignment of nucleotides using algorithms or computer programs and these techniques well known to those of skill in the art. In accordance with the invention other suitable polynucleotides for use may be obtained by the in silico identification of polynucleotides for regulatory sequences with at least 50% sequence identity, preferably at least 70%, 80% or 90% sequence identity, and most preferably 95%, 98% or 99% sequence identity with each other.

The invention provides a polynucleotide promoter sequence selected from SEQ ID NOs:1, 2, 3, 4, 5, 6, 7, 8, 9, 10 or 11, or the promoter sequence thereof, i.e., the sequence without the cloning sites. In one embodiment, a polynucleotide promoter sequence is provided which has at least 60% identity with any one of these polynucleotide promoter sequences. In another embodiment, a polynucleotide promoter sequence is provided which has at least 70% identity with any one of these polynucleotide promoter sequences. In an additional embodiment, a polynucleotide promoter sequence is provided which has at least 80% identity with any one of these polynucleotide promoter sequences. In a further embodiment, a polynucleotide promoter sequence is provided which has at least 90% identity with any one of these polynucleotide promoter sequences. In another embodiment, a polynucleotide promoter sequence is provided which has at least 95% identity with any one of these polynucleotide promoter sequences. In another embodiment, a polynucleotide promoter sequence is provided which has at least 98% identity with any one of these polynucleotide promoter sequences. In one embodiment, a promoter sequence herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs.

The invention provides a polynucleotide construct comprising an isolated promoter described herein, such as one selected from SEQ ID NOs:1, 2, 3, 4, 5, 6, 7, 8, 9, 10 or 11, or promoter portion thereof, operatively linked to a polypeptide-encoding sequence which is operatively linked to a transcriptional terminator. In one embodiment, an operable fragment, also termed a promoter portion herein, is about 400 base pairs up to about 1100 base pairs in length starting from the −1 position from the ATG codon. As used herein "up to" refers to the length of the promoter portion of the promoters set forth in the disclosed SEQ ID NOs. Thus, "up to" refers to the maximal length of the promoter sequence if less than 1100 nucleotides of the promoters of the disclosed SEQ ID NOs. In one embodiment, the polynucleotide construct enables efficient expression of a polypeptide in a fungal species selected from Pucciniomycotina and Ustilaginomycotina subphyla. The fungal species is preferably one selected from *Rhodosporidium, Rhodoturula, Ustilago, Pseudozyma,* or *Sporobolomyces* genus, the genome of which contains at least 50% C and G, preferably more than 60% C and G.

In one embodiment, the polynucleotide construct is inserted in a T-DNA vector, a shuttle vector, or in a fungal chromosome, wherein the polypeptide-encoding sequence contains at least 50% CG, preferably 60% CG and most preferably more than 80% CG.

In another embodiment, the polynucleotide promoter sequence contains at least one GAGGAG sequence, or it reverse complement sequence thereof. In another embodiment, the isolated promoter is operatively linked to a gene encoding antibiotic resistance enzyme, herbicide resistance enzyme, GFP, GUS, lacZ, terpene synthase, fatty acid desaturase, P450 cytochrome oxidase, glucanase, xylanase, mannanase, mannosidase, glucosidase, glucomannanase, xyluglucanase, hydroxymethylglutaryl-CoA synthase, hydroxymethylglutaryl-CoA reductase, acetyl-CoA C-acetyltransferase, mevalonate kinase, phosphomevalonate kinase, diphosphomevalonate decarboxylase, isopentenyl-diphosphate delta-isomerase, farnesyl diphosphate synthase, geranylgeranyl diphosphate synthase, methyl transferase, or glucosyl transferease, beta-carotenoid hydroxylase, beta-carotenoid oxidase.

In one embodiment, any transcriptional terminator operable in species of the fungi can be used. Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs) (Nagaya et al., 2010). NUEs usually reside approximately 30 bp away from a GU-rich region (Mogen et al., 1990; Mogen et al., 1992; Rothnie et al. 1994), known as far upstream elements (FUEs). The FUEs enhance processing at the polyadenylation sequence or cleavage site, which is usually a CA or UA in a U-rich region (Bassett, 2007). Within the terminator, elements exist that increase the stability of the transcribed RNA (Ohme-Takagi et al., 1993; Newman et al., 1993; Gutierrez et atl., 1999) and may also control gene expression (Ingelbrecht, 1989; An et al., 1989).

Nucleic acid hybridization, a technique well known to those of skill in the art of DNA manipulation, can be used to identify other suitable terminators. In accordance with the invention other suitable promoters for use may be obtained by the identification of terminators that selectively hybridize to the promoters described above by hybridization under low stringency conditions, moderate stringency conditions, or high stringency conditions. Selectively hybridizing sequences typically have at least 50% sequence identity, preferably at least 70%, 80% or 90% sequence identity, and most preferably 95%, 98% or 99% sequence identity with each other.

Database searches and homology searches of genome and nucleotide databases identify similar DNA or RNA molecules based on the alignment of nucleotides using algorithms or computer programs and these techniques well known to those of skill in the art. In accordance with the invention other suitable terminators for use may be obtained by the in silico identification of terminators for regulatory sequences with at least 50% sequence identity, preferably at least 70%, 80% or 90% sequence identity, and most preferably 95%, 98% or 99% sequence identity with each other.

A DNA of interest can be added to the polynucleotide construct. The DNA of interest is operatively linked to promoter and a terminator. Any promoter and terminator operable in species of the Pucciniomycotina and Ustilaginomycotina subphyla can be used. In some embodiments, the DNA of interest may be used to insert or modify metabolic pathways, such as fatty acid biosynthesis, lipid biosynthesis, triglyceride biosynthesis, and the like. The DNA of interest may be inserted into the genome of the fungal cells to enhance the bioconversion of renewable resources into high-value products, such as triglycerides, biodiesel, fatty alcohol, vitamins, biosurfactants, lactone, terpenoid and the like.

A polynucleotide construct may be introduced directly into the genomic DNA of the fungal cell using techniques such as electroporation and microinjection of plant cell protoplasts, or the polynucleotide constructs can be introduced directly to fungal tissue using ballistic methods, such as DNA particle bombardment. Alternatively, the polynucleotide constructs may be combined with suitable T-DNA flanking regions and introduced into a conventional *Agrobacterium tumefaciens* host vector. The virulence functions of the *Agrobacterium tumefaciens* host will direct the insertion of the construct into the fungal cell DNA when the cell is infected by the bacteria. Thus, any method, which provides for effective transformation/transfection may be employed. See, for example, U.S. Pat. Nos. 7,241,937, 7,273,966 and 7,291,765 and U.S. Patent Application Publication Nos. 2007/0231905 and 2008/0010704 and references cited therein. See also, International Published Application Nos. WO 2005/103271 and WO 2008/094127 and references cited therein.

The transformed fungi are transferred to standard growing media (e.g., solid or liquid nutrient media, grain, vermiculite, compost, peat, wood, wood sawdust, straw, etc.) and grown or cultivated in a manner known to the skilled artisan.

After the polynucleotide is stably incorporated into transformed fungi, it can be transferred to other fungi by sexual crossing. Any of a number of standard breeding techniques can be used, depending upon the species to be crossed.

It may be useful to generate a number of individual transformed fungi with any recombinant construct in order to recover fungi free from any positional effects. It may also be preferable to select fungi that contain more than one copy of the introduced polynucleotide construct such that high levels of expression of the recombinant molecule are obtained.

It may be desirable to produce fungal lines that are homozygous for a particular gene if possible in the particular species. In some species this is accomplished by the use monosporous cultures. By using these techniques, it is possible to produce a haploid line that carries the inserted gene and then to double the chromosome number either spontaneously or by the use of colchicine. This gives rise to a fungus that is homozygous for the inserted gene, which can be easily assayed for if the inserted gene carries with it a suitable selection marker gene for detection of fungi carrying that gene. Alternatively, fungi may be self-fertilized, leading to the production of a mixture of spores that consists of, in the simplest case, three types, homozygous (25%), heterozygous (50%) and null (25%) for the inserted gene. Although it is relatively easy to score null fungi from those that contain the gene, it is possible in practice to score the homozygous from heterozygous fungi by Southern blot analysis in which careful attention is paid to the loading of exactly equivalent amounts of DNA from the mixed population, and scoring heterozygotes by the intensity of the signal from a probe specific for the inserted gene. It is advisable to verify the results of the Southern blot analysis by allowing each independent transformant to self-fertilize, since additional evidence for homozygosity can be obtained by the simple fact that if the fungi was homozygous for the inserted gene, all of the subsequent fungal lines from the selfed individual will contain the gene, while if the fungus was heterozygous for the gene, the generation grown from the selfed seed will contain null fungal lines. Therefore, with simple selfing one can select homozygous fungal lines that can also be confirmed by Southern blot analysis.

Creation of homozygous parental lines makes possible the production of hybrid fungus and spores that will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The practice of the present invention employs, unless otherwise indicated, conventional techniques of chemistry, molecular biology, microbiology, recombinant DNA, genetics, immunology, cell biology, cell culture and transgenic biology, which are within the skill of the art. See, e.g., Maniatis et al., 1982, *Molecular Cloning* (Cold Spring Harbor Laboratory Press, Cold Spring Harbor, New York); Sambrook et al., 1989, *Molecular Cloning*, 2nd Ed. (Cold Spring Harbor Laboratory Press, Cold Spring Harbor, New York); Sambrook and Russell, 2001, *Molecular Cloning*, 3 rd Ed. (Cold Spring Harbor Laboratory Press, Cold Spring Harbor, New York); Ausubel et al., 1992), *Current Protocols in Molecular Biology* (John Wiley & Sons, including periodic updates); Glover, 1985, *DNA Cloning* (IRL Press, Oxford); Russell, 1984, *Molecular biology of plants: a laboratory course manual* (Cold Spring Harbor Laboratory Press, Cold Spring Harbor, N.Y.); Anand, *Techniques for the Analysis of Complex Genomes*, (Academic Press, New York, 1992); Guthrie and Fink, *Guide to Yeast Genetics and Molecular Biology* (Academic Press, New York, 1991); Harlow and Lane, 1988, *Antibodies*, (Cold Spring Harbor Laboratory Press, Cold Spring Harbor, New York); *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, Blackwell Scientific Publications, Oxford, 1988; Fire et al., *RNA Interference Technology: From Basic Science to Drug Development*, Cambridge University Press, Cambridge, 2005; Schepers, *RNA Interference in Practice*, Wiley-VCH, 2005; Engelke, *RNA Interference (RNAi): The Nuts & Bolts of siRNA Technology*, DNA Press, 2003; Gott, *RNA Interference, Editing, and Modification: Methods and Protocols (Methods in Molecular Biology)*, Human Press, Totowa, N.J., 2004; Sohail, *Gene Silencing by RNA Interference: Technology and Application*, CRC, 2004.

EXAMPLES

The present invention is described by reference to the following Examples, which are offered by way of illustration and are not intended to limit the invention in any manner. Standard techniques well known in the art or the techniques specifically described below were utilized.

Example 1

Culture of Microbial Strains and Basic Molecular Methods

*Rhodosporidium toruloides* strain ATCC10657 (referred to as Rt1), and *Rhdotorula glutinis* strain ATCC204091 (referred to as Rg2), *Pseudozyma aphidis* ATCC32657, were sourced from the American Type Culture Collections (ATCC). *Sporobolomyces roseus* FGSC 10293 (IAM13481) and *Rhodotorula graminis* WP1 (FGSC WP1) (referred to as Rg3) were obtained from Fungal Genetics Stock Center (University of Missouri, USA). *Ustilago maydis* strain and *Agrobacterium tumefaciens* strain AGL-1 have been described (Ji et al., 2010; Lazo et al., 1991). *Escherichia coli* strain XL1-Blue was used for routine plasmid manipulation and amplification. Fungal strains were cultured at 28° C. in YPD broth (1% yeast extract, 2% peptone, 2% glucose) or on solid potato-dextrose agar (PDA). *A. tumefaciens* was cultured at 28° C. in either liquid or solid 2YT medium (1.6% tryptone, 1% yeast extract, 0.5% NaCl). *E. coli* was grown in LB broth or on solid LB agar.

Genomic DNA was extracted based on the method described for *U. maydis* (Ji et al., 2010) with some modifications. Briefly, the cell culture at exponential phase was collected and washed with 1 M sorbitol. The cells were resuspended in 0.1 ml of SCS buffer (1 M sorbitol, 20 mM sodium citrate, pH 5.8) and supplemented with glass beads (1 mm in diameter, Sigma-Aldrich, USA). Cells lysis made by vortexing and genomic DNA was isolated after phenol/chloroform extraction and ethanol precipitated. The extracted DNA was quantified with NanoDrop® ND-1000 Spectrophotometer (Nanodrop Technologies, USA) and DNA quality analyzed by agarose gel electrophoresis.

Example 2

*Agrobacterium tumefaciens*-Mediated Transformation (ATMT)

ATMT was performed essentially as described previously for *R. toruloides, S. roseus, U maydis* and *Pseudozyma aphidis*(Ji, et al., 2010; Liu, et al, 2012). Co-culturing of fungal cells and *Agrobacterium* donors were done at pH5.6, 24° C. for 2.5-3 days on nylon membranes and selection was done on YPD plates containing 300 µg/ml cefotaxime and 150-300 µg/ml (150 µg/ml for *R. toruloides, R. glutinis*, and 300 µg/ml for *P. aphidis* and *S. roseus*) hygromycin B at 28° C. for 3-5 days.

Example 3

Cloning of Promoters

Based on the published EST sequence abundance in various media (Ho et al, 2007), we selected a number of genes (Table 1) as potential source of strong promoters for *Rhodosporidium* and *Rhodotorula*. Other candidate genes include those encoding proteins in the fatty acid biosynthesis in *Rhodosporidium* and *Rhodotorula*, e.g., acetyl-CoA synthase (ACC1), acyl-CoA carrier protein (ACP1), pyruvate decarboxylase (PDC1) and nitrate regulated gene (NAR1). *Ustilago maydis* CDS sequences were searched against the *Rhodosporidium* and *Rhodotorula* genome database.

TABLE 1

Candidate Genes with Strong Promoter

| Complete Medium* | carbon starvation media* | Nitrogen starvation media* | dormant teliospore* | Description | MUMDB ID |
|---|---|---|---|---|---|
| 7 | 18 | 22 | 3 | glyceraldehyde 3-phosphate dehydrogenase | um02491 |
| 35 | 54 | 22 | 11 | probable TAL1 - transaldolase | um04138 |
| 8 | 12 | 6 | 0 | probable Actin | um11232 |
| 107 | 79 | 65 | 32 | probable ubiquitin/ribosomal protein S27a fusion protein | um04588 |
| 146 | 54 | 16 | 8 | probable FPR1 - peptidyl-prolyl cis-trans isomerase, FK506-binding protein | um11054 |
| 35 | 37 | 14 | 17 | probable CPR1 - cyclophilin (peptidylprolyl isomerase) | um03726 |
| 48 | 13 | 29 | 4 | probable translation elongation factor eEF-1 alpha chain | um00924 |
| 0 | 0 | 0 | 2 | probable PDC1 - pyruvate decarboxylase, isozyme 1 | um03994 |
| 17 | 6 | 11 | 1 | probable ENO1 - enolase I (2-phosphoglycerate dehydratase) | um03356 |

Note:
*Numbers indicate total hits in the EST library of the respective medium.

To define the 3' end of the promoters, 5' RACE were performed using BD SMARTer™ RACE cDNA Amplification Kit (Clontech, California, USA) according to the manufacturer's instruction. Promoter DNA fragments were obtained by PCR using a 3' end primer that is designed at the first ATG in the 5' untranslated regions, usually with an overlapping NcoI (CCATGG) or BspHI (TCATGA) site at the ATG codon. BamHI is used if the DNA sequence contains both NcoI and BspHI sites. 5' Primers were designed 1-2 kb from the ATG. The primers used are listed in Table 2. The PCR fragments were digested with corresponding enzymes, cloned in pPN006 or pRH2031 (FIG. 1), which is a T-DNA vector containing the RtGPD1::RtGFP: nos cassette (Liu et al, 2012).

TABLE 2

Cloning of Selected Promoters

| SEQ ID NO: | Promoter name | Origin | Length (bp) | 5' PCR primers (SEQ ID NO:) | 3' PCR primer (SEQ ID NO:) |
|---|---|---|---|---|---|
| 1 | Rg2TEF1 | R. glutinis ATCC 204091 translation elongation factor | 1017 | AAAGGTACCGTGCGAGAAG AAGCGAGGC (13) | AAACCATGGTTCCCCC CCAGTACACAGTACAG TA (14) |
| 2 | Rg3TEF1 | R. graminis strain WP1 translation elongation factor | 946 | AAAGGTACCCATGCTGCTG CTGCCCCTCA (15) | ATACCATGGTGGATGA AGTGAGATTCGAGTG (16) |
| 3 | Rg3S27 | R. graminis strain WP1 ribosomal protein S27 | 1464 | AAAGGTACCCAAAGGGAGA GGAGCGGGCG (17) | AAACCATGGTGACCTA CGCCTACACAAGGGTG C (18) |
| 4 | Rg2ACP1 | R. glutinis ATCC 204091 acyl-CoA carrier protein | 1321 | AAAGGTACCTGAGCGGGCG AGCCGCGAG (19) | aaaTCATGACTGAACA AAGTTTTCCTGCGGCG C (20) |
| 5 | Rg2NAR1 | R. glutinis ATCC 204091 nitrate reductase | 1499 | AAAGGTACCGCTCATCATC GAGCGAGGGCAG (21) | AAACCATGGCGGCGGG TGATTCTTCTTGGTTC (22) |
| 6 | Rg2ENO1 | R. ATCC 204091 enolase(phosphopyruvate hydratase) | 1596 | gactagtcGCCAGGGAACG CAGAGAAGG (23) | aaaccatgGCTGTGAG AGGAGTATCGCAG (24) |
| 7 | Rg2PDC1 | R. glutinis ATCC 204091 pyruvate decarboxylase | 1391 | gactagtcGGCGAAGAGGA GGGGTGTTAGG (25) | aaaggatccgccatTGCGGT TCAAAGGCTGGGCG (26) |
| 8 | Rg3ENO1 | R. graminis strain WP1 enolase(phosphopyruvate hydratase) | 1500 | gactagtCGTGCAGAAGGA ACCCGAGGAG (27) | aaaccatgGCGAGGCGAGAG GGGTTGAG (28) |
| 9 | Rg3PDC1 | R. graminis strain WP1 pyruvate decarboxylase | 1500 | gactagtcGGGAGGATTGA TGATCGGGTTGC (29) | aaacCATGGTGGTCGAGCTT GTGAGG (30) |
| 10 | Rg3PPI | R. graminis strain WP1 peptidylprolyl isomerase | 1222 | AAAGGTACCGCGAGGGGAA GGGCAGGAGAGTCG (31) | AAACCATGGTCGGACGGTGG GAAGGGGGGGGA (32) |
| 11 | Rg3TAL1 | R. graminis strain WP1 transaldolase | 1507 | AAAGGTACCACTACCTCGT CACGACCCAGGGTG (33) | AAACCATGGTGTAGGTAGCT GCGGCGGGT (34) |
| 12 | Rg2ACC1 | R. glutinis ATCC 204091 acetyl-CoA synthase | 1646 | AAAGGCGCGCCTGAAGCTG TACATCGAGGTGGAC (35) | aaaCCATGGTCCCACAATCA GTAGTTGTCCTCGGAAG (36) |

Example 4

Promoter Activity in *Rhodosporidium* in Lipid Production Medium

The promoter GFP reporter constructs were transformed to *Rhodosporidium toruloides* ATCC 10657 by the ATMT method. The transformed colonies (>100) were pooled, cultured in YPD medium with 150 μg/ml hygromycin B and 300 μg/ml cefataxome and diluted to about 0.1 OD600 in lipid production medium [10 mM K2HPO4-KH2PO4, (pH6.13), 4 g/L yeast extract, 0.3 g/L urea, 0.1 g/L Na2SO4, 10 mg/L each of tyrosine, valine and vitamin B (B1+B6), 8% glucose] with no antibiotics added. Strains were cultured at 28° C. with shaking (280 rpm) 2 days and then dilute to about 0.1 OD600 for 24 hours and the cultures were adjusted to 0.6 OD600 units before subjecting to florescence measurement in a Tecan M200 reader using 476 nM as excitation wavelength, and 509 nM as emission wavelength; gain value 100. The florescence intensity were normalized to OD600 and subtracted against non-transformed cell cultures under the same conditions. Rg3 TAL1 is weak while Rg2ACC1 showed no obvious activity (Table 3). Transformants of the Rg2A CC1 reporter in *Rhodosporidium glutinis* ATCC 90781 showed no GFP florescence was cultured a nitrogen-limited medium (glucose 70 g/l, yeast extract 0.75 g/l, (NH4)2SO4 0.1 g/l, KH2PO4 1.0 g/l, MgSO4.7H2O 1.5 g/l, pH 5.6) for 24 hr either (not shown). Promoter RtGPD1 is set forth in SEQ ID N:38.

TABLE 3

Relative GFP Fluorescence of Selected Promoters in *Rhodosporidium toruloides*

| Promoter | Rg2TEF1 | Rg3TEF1 | Rg3TAL1 | Rg3S27 | Rg3PPI | Rg2ENO1 | Rg2ACC1 | RtGPD1 |
|---|---|---|---|---|---|---|---|---|
| Fluorescence reading | 183 | 616 | 83 | 316 | 566 | 383 | 0 | 1100 |

Example 5

Promoter Activity in N-Rich and N-Free Medium in Rhodosporidium, Pseudozyma, Ustilago and Sporobolomyces A selected set of promoter GFP reporter constructs were transformed by the ATMT method to *Rhodosporidium toruloides* ATCC 10657, *Ustilago maydis* L8, *Pseudozyma aphidis* ATCC32657 and *Sporobotomyces roseus* FGSC 10293. The transformed colonies (>100) were pooled, cultured in YPD medium with 150 μg/ml (or 300 μg/ml for *Pseudozyma aphidis*) hygromycin B and 300 μg/ml cefataxome for 2 days at 28° C. and diluted to about 0.1 OD600 in YNB Medium and also in YNB N-Medium (both medium with 5% gluocose.) and continued culture for 1-3 days with shaking. OD600 and GFP florescence were measured with Tecan infinite200. The GFP fluorescence intensity (normalized against the OD600) is listed in Tables 4-11. Promoters Umgpd1, RtGPD1, Rg3GPD1, Rg2FAD1 and SrGPD1 are set forth in SEQ IN NOs:37, 38, 39, 40 and 41, respectively. The isolation of these promoters is described in WO 2012/169969.

TABLE 4

Fluoresence Intensity in *R. toruloides* ATCC 10657 in YNB Medium

|  | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 67098.1 ± 4810.2 | 493314.2 ± 17949.6 | 315280.7 ± 13486.8 | 822714.3 ± 29975.4 | 76162.8 ± 5196.2 | 1229511.5 ± 38057.0 | 439906.8 ± 20026.2 | 310853.1 ± 11379.8 |
| Day 2 | 90051.8 ± 5580.0 | 324001.3 ± 15528.4 | 138885.1 ± 5578.8 | 328422.2 ± 13168.4 | 77194.7 ± 5304.6 | 960118.3 ± 35167.0 | 195357.6 ± 14536.8 | 49159.7 ± 2473.8 |
| Day 3 | 125629.1 ± 5884.6 | 109829.4 ± 5871.2 | 71034.5 ± 3793.6 | 391254.0 ± 15650.6 | 72916.9 ± 5191.4 | 1080769.4 ± 37277.4 | 186096.4 ± 15397.2 | 69658.8 ± 2717.4 |

|  | Rg3PDC1 | Umgpd1 | RtGPD1 | Rg3GPD1 | Rg2FAD1 | SrGPD1 |
|---|---|---|---|---|---|---|
| Day 1 | 524990.1 ± 19316.2 | 185894.4 ± 5956.8 | 647267.9 ± 17825.0 | 482273.0 ± 17080.6 | 790204.6 ± 26581.6 | 94929.5 ± 3664.8 |
| Day 2 | 318157.8 ± 13705.8 | 23430.4 ± 11392.6 | 470829.4 ± 19049.2 | 302113.7 ± 27780.8 | 622505.2 ± 24257.0 | 57888.5 ± 3134.6 |
| Day 3 | 179610.3 ± 7379.4 | 52504.2 ± 2197.4 | 417595.6 ± 16078.8 | 294063.5 ± 16996.2 | 678405.8 ± 25364.6 | 72393.3 ± 3358.4 |

TABLE 5

Fluoresence Intensity in *R. toruloides* ATCC 10657 in YNB N-free Medium

|  | Rg2TEF | Rg3TEF1 | Rg3S27 | Rg2ACP1 | Rg2NAR1 | Rg2ENO1 | Rg2PDC1 | Rg3ENO |
|---|---|---|---|---|---|---|---|---|
| Day 1 | 70881.8 ± 5110.9 | 380951.5 ± 18050.3 | 365547.6 ± 13587.5 | 815919.4 ± 30076.1 | 272301.0 ± 5296.9 | 1424622.6 ± 38157.7 | 446260.0 ± 20126.9 | 146494.1 ± 11480.5 |
| Day 2 | 85225.0 ± 5880.7 | 154658.6 ± 15629.1 | 229116.8 ± 5979.5 | 194767.0 ± 13269.1 | 96375.2 ± 5405.3 | 1023479.6 ± 35267.7 | 189373.9 ± 14637.5 | 87625.2 ± 2574.5 |
| Day 3 | 101884.6 ± 6085.3 | 75616.7 ± 5971.9 | 131082.7 ± 3894.3 | 274152.1 ± 15751.3 | 49724.9 ± 5292.1 | 1045808.5 ± 37378.1 | 175901.0 ± 15497.9 | 41721.8 ± 2818.1 |

|  | Rg3PDC1 | Umgpd1 | RtGPD1 | Rg3GPD1 | Rg2FAD1 | SrGPD1 |
|---|---|---|---|---|---|---|
| Day 1 | 521271.4 ± 19416.9 | 179467.0 ± 6057.5 | 798469.1 ± 17925.7 | 543617.9 ± 17181.3 | 1046580.2 ± 26682.3 | 208402.0 ± 3765.5 |
| Day 2 | 229565.0 ± 13806.5 | 70298.9 ± 11493.3 | 559941.0 ± 19149.9 | 325267.7 ± 27881.5 | 729764.3 ± 24357.7 | 74769.4 ± 3235.3 |
| Day 3 | 116966.8 ± 7480.1 | 42892.0 ± 2298.1 | 240704.2 ± 16179.5 | 143840.6 ± 17096.9 | 495414.9 ± 25564.6 | 27930.9 ± 3459.1 |

TABLE 6

Fluoresence Intensity in *P. aphidis* in YNB Medium

|  | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 20710.7 ± 535.5 | 24954.1 ± 1347.7 | 17864.7 ± 903.2 | 25694.5 ± 1084.7 | 11741.6 ± 577.1 | 15870.6 ± 783.5 | 21807.7 ± 790.4 | 19768.3 ± 978.4 |
| Day 2 | 5617.3 ± 268.1 | 7829.7 ± 612.5 | 4804.2 ± 403.4 | 7541.3 ± 629.4 | 3854.7 ± 311.2 | 4634.5 ± 306.2 | 6430.8 ± 595.9 | 5748.1 ± 519.0 |
| Day 3 | 3738.0 ± 173.8 | 3980.9 ± 298.1 | 3106.8 ± 240.7 | 3793.1 ± 699.3 | 1679.0 ± 137.9 | 2504.5 ± 301.5 | 3504.2 ± 410.4 | 3165.2 ± 396.5 |

|  | Rg3PDC1 | Umgpd1 | RtGPD1 | Rg3GPD1 | Rg2FAD1 | SrGPD1 |
|---|---|---|---|---|---|---|
| Day 1 | 27733.8 ± 986.7 | 22180.7 ± 1009.0 | 29319.0 ± 465.9 | 37495.4 ± 1774.8 | 16309.0 ± 215.5 | 23103.0 ± 1455.1 |

TABLE 6-continued

Fluoresence Intensity in *P. aphidis* in YNB Medium

|  | | | | | | |
|---|---|---|---|---|---|---|
| Day 2 | 8123.9 ± 617.0 | 6537.3 ± 584.8 | 9876.9 ± 803.1 | 9713.0 ± 709.4 | 4859.7 ± 615.0 | 7830.9 ± 752.6 |
| Day 3 | 4602.1 ± 780.2 | 3260.7 ± 324.1 | 4542.3 ± 154.2 | 5781.1 ± 478.1 | 2671.1 ± 167.1 | 3900.5 ± 290.0 |

TABLE 7

Fluoresence Intensity in *P. aphidis* YNB N-free Medium

| | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 4030.5 ± 455.2 | 17201.3 ± 1145.5 | 4757.5 ± 367.8 | 14666.9 ± 322.0 | 5485.1 ± 490.5 | 13203.8 ± 466.0 | 10218.7 ± 271.8 | 12705.6 ± 831.7 |
| Day 2 | 5247.5 ± 214.5 | 14281.5 ± 290.0 | 7093.2 ± 322.7 | 7835.6 ± 503.6 | 6845.8 ± 549.0 | 6734.8 ± 245.0 | 5801.6 ± 476.7 | 3302.7 ± 415.2 |
| Day 3 | 5762.8 ± 530.3 | 12371.9 ± 223.6 | 1983.5 ± 180.5 | 2564.9 ± 224.5 | 2014.3 ± 203.4 | 2791.4 ± 226.1 | 2013.8 ± 187.8 | 5876.3 ± 297.4 |

| | | | Rg3PDC1 | Umgpd1 | RtGPD1 | Rg3GPD1 | Rg2FAD1 | SrGPD1 |
|---|---|---|---|---|---|---|---|---|
| | | Day 1 | 11338.6 ± 338.7 | 9034.5 ± 257.7 | 11511.6 ± 396.1 | 9322.7 ± 208.6 | 13410.0 ± 383.1 | 21144.1 ± 936.9 |
| | | Day 2 | 9382.1 ± 193.6 | 13731.3 ± 467.8 | 10564.5 ± 142.5 | 10390.4 ± 567.5 | 16069.0 ± 492.0 | 16013.3 ± 202.1 |
| | | Day 3 | 5874.1 ± 585.2 | 5004.3 ± 243.1 | 7856.3 ± 215.7 | 9851.7 ± 233.6 | 12774.0 ± 225.3 | 14045.7 ± 317.5 |

TABLE 8

Fluoresence Intensity in *U. maydis* L8 in YNB Medium

| | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 4497.4 ± 405.1 | 31255.7 ± 1974.8 | 8744.3 ± 743.4 | 16705.1 ± 987.7 | 5663.0 ± 598.1 | 10351.3 ± 608.5 | 17224.0 ± 813.1 | 18699.4 ± 689.9 |
| Day 2 | 2237.4 ± 190.0 | 20291.8 ± 1064.2 | 12961.1 ± 789.4 | 7046.8 ± 584.2 | 1899.9 ± 252.3 | 3508.0 ± 183.5 | 1948.5 ± 268.4 | 4185.3 ± 236.9 |
| Day 3 | 728.7 ± 142.3 | 29221.7 ± 1935.6 | 2132.4 ± 196.8 | 1651.0 ± 125.3 | 6453.6 ± 295.7 | 1885.2 ± 138.7 | 1610.0 ± 198.6 | 10261.0 ± 858.7 |

| | | | Rg3PDC1 | Umgpd1 | RtGPD1 | Rg3GPD1 | Rg2FAD1 | SrGPD1 |
|---|---|---|---|---|---|---|---|---|
| | | Day 1 | 30749.5 ± 1658.1 | 12977.4 ± 978.4 | 38101.5 ± 1012.5 | 16539.8 ± 540.3 | 35361.2 ± 1290.8 | 20121.3 ± 932.4 |
| | | Day 2 | 10692.2 ± 452.9 | 14498.0 ± 1096.3 | 33043.3 ± 924.6 | 5729.0 ± 290.4 | 13483.6 ± 728.5 | 13639.8 ± 567.3 |
| | | Day 3 | 13449.8 ± 689.7 | 10667.8 ± 108.7 | 37663.7 ± 839.4 | 4328.0 ± 498.1 | 19667.2 ± 1282.3 | 7559.5 ± 219.2 |

TABLE 9

Fluoresence Intensity in *U. maydis* L8 in YNB N-free Medium

| | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 2736.3 ± 195.3 | 23444.3 ± 1674.3 | 4848.0 ± 743.4 | 14420.4 ± 785.7 | 4965.9 ± 291.7 | 3393.2 ± 258.4 | 5099.7 ± 363.5 | 13592.6 ± 907.9 |
| Day 2 | 4635.9 ± 200.5 | 22335.2 ± 984.7 | 11189.0 ± 628.3 | 12643.8 ± 784.1 | 8929.3 ± 332.9 | 8782.8 ± 384.2 | 6278.8 ± 435.4 | 16443.4 ± 1023.5 |
| Day 3 | 4778.9 ± 242.3 | 21945.0 ± 1531.6 | 5243.9 ± 171.1 | 3563.5 ± 105.6 | 1052.9 ± 99.3 | 402.1 ± 138.7 | 2136.7 ± 108.1 | 3832.4 ± 251.7 |

| | | | Rg3PDC1 | Umgpd1 | RtGPD1 | Rg3GPD1 | Rg2FAD1 | SrGPD2 |
|---|---|---|---|---|---|---|---|---|
| | | Day 1 | 20887.7 ± 1043.2 | 8457.1 ± 275.2 | 36784.6 ± 909.4 | 5161.0 ± 204.5 | 27948.4 ± 1073.6 | 19682.9 ± 1136.5 |
| | | Day 2 | 18643.1 ± 853.6 | 15615.6 ± 1001.7 | 31362.0 ± 931.9 | 9944.7 ± 300.1 | 19059.7 ± 839.1 | 10507.5 ± 509.5 |
| | | Day 3 | 10741.0 ± 619.2 | 5416.3 ± 157.7 | 22029.0 ± 791.3 | 5116.4 ± 332.8 | 14070.9 ± 812.8 | 5509.8 ± 293.1 |

TABLE 10

Fluoresence Intensity in S. roseus for in YNB Medium

|  | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 34433.7 ± 2961.3 | 62781.0 ± 5013.6 | 49396.6 ± 3965.7 | 35726.2 ± 3012.6 | 44850.3 ± 7639.8 | 54393.9 ± 2013.6 | 45625.4 ± 3968.1 | 75257.5 ± 3086.3 |
| Day 2 | 7223.1 ± 1025.8 | 7997.9 ± 1169.4 | 5486.4 ± 1032.6 | 11336.9 ± 698.1 | 7453.9 ± 854.1 | 16829.3 ± 852.3 | 7401.2 ± 897.5 | 7108.0 ± 1087.6 |
| Day 3 | 9874.2 ± 1356.9 | 6212.6 ± 1598.7 | 7978.3 ± 1648.1 | 6425.8 ± 963.7 | 8653.9 ± 1587.5 | 9632.8 ± 897.6 | 9013.8 ± 1258.4 | 9898.4 ± 1698.7 |

|  | Rg3PDC1 | Umgpd1 | RtGPD1 | Rg3GPD1 | Rg2FAD1 | SrGPD2 |
|---|---|---|---|---|---|---|
| Day 1 | 75080.8 ± 3015.7 | 61607.3 ± 2345.1 | 115602.4 ± 4598.7 | 36185.9 ± 2845.2 | 55143.4 ± 5423.9 | 76783.0 ± 1946.3 |
| Day 2 | 7110.1 ± 521.7 | 13471.3 ± 369.3 | 7832.5 ± 496.8 | 6434.0 ± 963.4 | 10613.7 ± 1015.8 | 24326.0 ± 876.5 |
| Day 3 | 9985.6 ± 765.1 | 8013.7 ± 965.4 | 11231.1 ± 1065.8 | 4931.2 ± 1259.8 | 7469.8 ± 1345.9 | 16036.7 ± 1897.4 |

TABLE 11

Fluoresence Intensity in S. roseus in YNB N-free Medium

|  | Rg2TEF1 | Rg3TEF1 | Rg3S27 | Rg2ACP1 | Rg2NAR1 | Rg2ENO1 | Rg2PDC1 | Rg3ENO1 |
|---|---|---|---|---|---|---|---|---|
| Day 1 | 30415.8 ± 2111.3 | 38195.6 ± 2163.4 | 34075.9 ± 3115.7 | 37998.4 ± 2162.6 | 39594.0 ± 4678.3 | 38138.8 ± 1163.6 | 25733.8 ± 3118.1 | 43722.6 ± 2236.3 |
| Day 2 | 6135.6 ± 905.8 | 9358.5 ± 1049.4 | 10507.2 ± 912.6 | 13226.8 ± 578.1 | 9190.2 ± 734.1 | 11034.9 ± 732.3 | 5662.3 ± 777.5 | 11550.1 ± 967.6 |
| Day 3 | 2698.7 ± 1206.9 | 5401.2 ± 1448.7 | 3012.9 ± 1498.1 | 6968.6 ± 813.7 | 2165.8 ± 1437.5 | 2857.4 ± 747.6 | 3541.9 ± 1108.4 | 4986.2 ± 1548.4 |

|  | Rg3PDC1 | Umgpd1 | RtGPD1 | Rg3GPD1 | Rg2FAD1 | SrGPD2 |
|---|---|---|---|---|---|---|
| Day 1 | 42986.2 ± 2165.7 | 53744.0 ± 1495.1 | 60102.2 ± 2365.9 | 49641.6 ± 1995.2 | 45162.3 ± 4573.9 | 47127.7 ± 1096.3 |
| Day 2 | 11959.0 ± 401.7 | 7691.8 ± 249.3 | 12012.4 ± 376.8 | 10303.5 ± 843.4 | 10948.1 ± 895.8 | 14795.5 ± 756.5 |
| Day 3 | 4879.3 ± 615.1 | 5897.1 ± 815.4 | 7854.3 ± 915.8 | 4013.7 ± 1109.8 | 3946.5 ± 1195.9 | 9154.6 ± 1747.4 |

Example 6

Identification of Critical Elements for Strong Promoters

Promoter sequences of Rg3TEF1, Rg3S27, Rg2ACP1, Rg2ENO1, Rg2PDC1, Rg3PDC1 and Rg2FAD1 (stearoyl-CoA delta-9 desaturase) were subjected to promoter motif scanning using the Gibbs Motif Sampler at http://ccmbweb.ccv.brown.edu/cgi-bin/gibbs.12.pl?data13 type=DNA&layout=advancedprgm&restore=var/www/cgi-bin/euk.def.txt.

Figure 2:
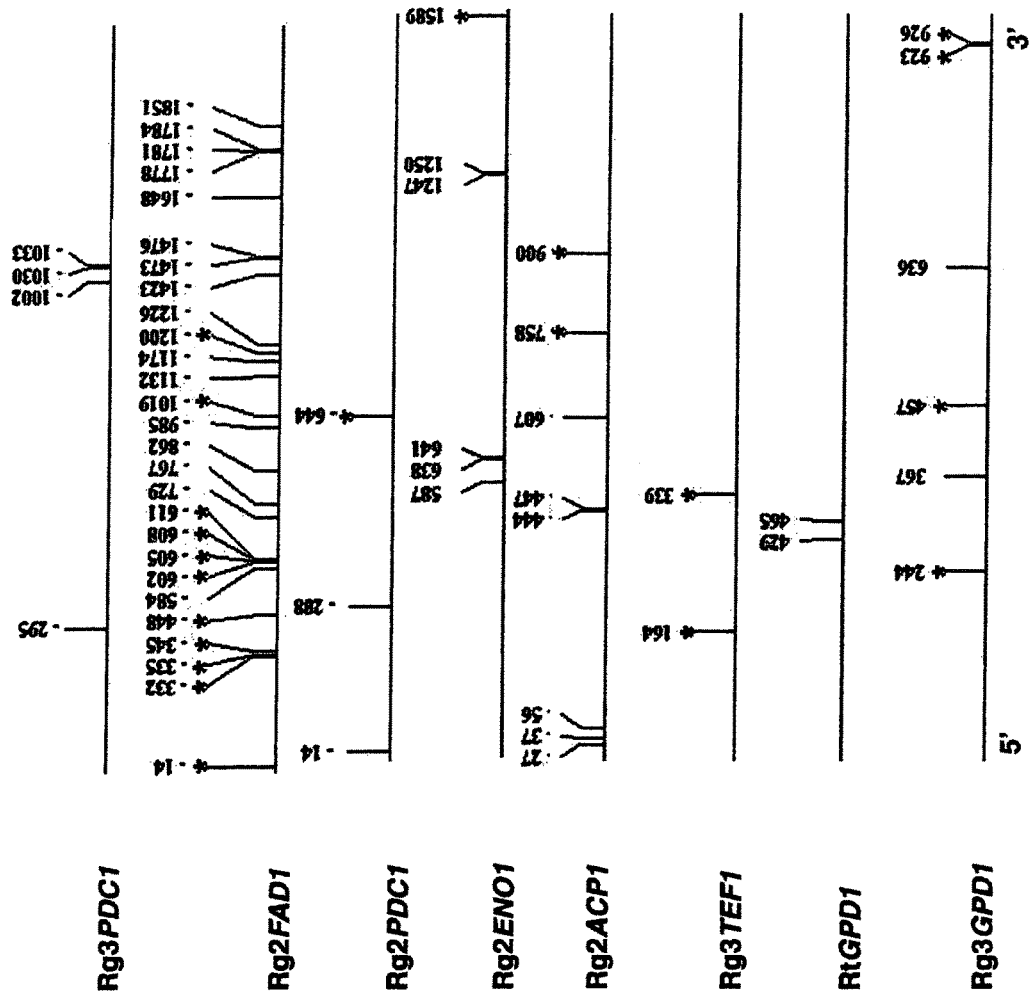
FIG. 2 shows the location of GAGGAG motifs. Vertical lines with * indicate GAGGAG motifs in sense orientation the remaining lines are in the antisense orientation.

A conserved motif sharing the GAGGAG core sequence were found in each promoter. Noticeably, Rg2FAD1 promoter, which is among the strongest promoters contains the largest number of the motif. (FIG. 2).

Example 7

Nested Deletion of Rg2FAD1 and Rg2ENO1 Promoters

Figure 3:
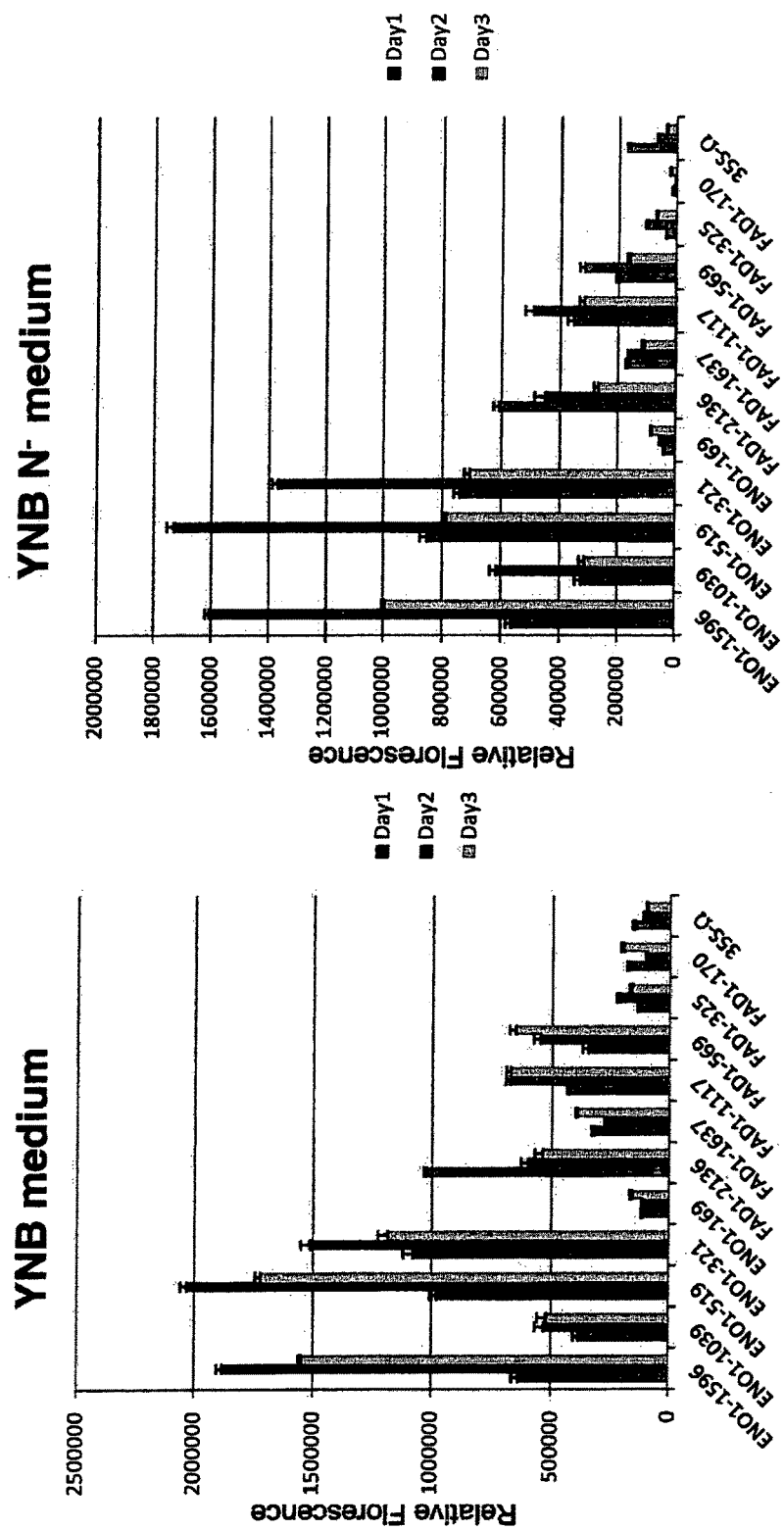
FIG. 3 shows the relative florescence of RtGFP driven by ENO1 and FAD1 promoters of various lengths, which is defined as the nucleotide number starting from the first nucleotide from the putative translation initiation codon (ATG) up to the point of 5' end, excluding the restriction sites added. The promoters showed similar trend in YNB and YNB nitrogen-free ($N^{31}$) media. 35S-Ω is a basic promoter containing the cauliflower mosaic visus 35S gene promoter starting from the TATA box down to the −1 position of 5' UTR and the omega translation enhancer sequence of Tobacco mosaic virus (TMV) inserted immediate upstream of RtGFP. Background florescence of non-transformed strain (*R. toruloides* ATCC 10657) has been subtracted in all values.

The full length Rg2ENO1 and Rg2FAD1 (stearoyl-CoA delta-9 desaturase gene) promoter GFP reporter constructs in pRH2031 were modified to have serially shortened promoters. This was done replacing the promoter with PCR fragments about 300, 500, 1000 and 1500 bp version of the promoter. All 5' primers included a SpeI cutting site while the 3' primer contains a NcoI cutting site. Constructs were transformed by the ATMT method to *Rhodosporidium toruloides* ATCC 10657. The transformed colonies (>500) were pooled, cultured in YNB medium with 150 µg/ml hygromycin B and 300 µg/ml cefataxome for 2 days at 28° C. and diluted to about 0.1 $OD_{600}$ in YNB Medium and also in YNB N⁻ Medium (both medium with 5% glucose.) and continued culture for 24 hours with shaking. The cultures reached $OD_{600}$ 0.2 units in YNB N+ and YNB N⁻ media. GFP florescence were measured with Tecan infinite M200. Gain parameter is consistently set at 85; Excitation and Emission wavelength are 476, 509. The GFP fluorescence intensity (normalized against the OD600) is listed in FIG. 3, which shows that minimal length of the ENO1 promoter for the optimal expression of reporter gene is approximately 320 to 520 bp, whereas the FAD1 promoter requires approximately 570 to 1120 bp.

Example 8

Nested Deletion of 519 bp Rg2ENO1 Promoter

Figure 4:
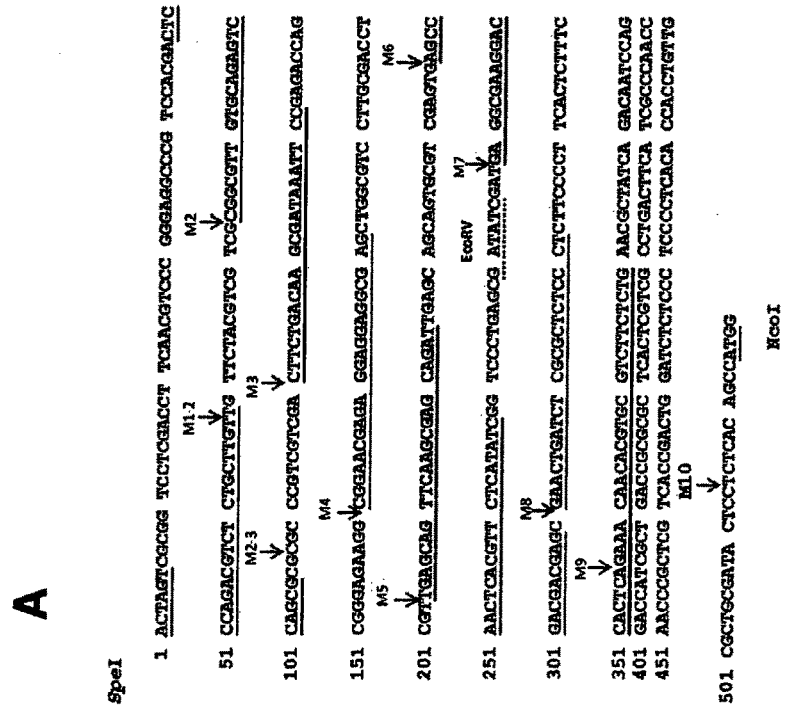
FIG. 4A shows details of the 519 bp Rg2ENO1 promoter sequence. Arrows indicate the positions of 5' ends of various deletions. The sequence is set forth in SEQ ID NO:42.
FIG. 4B shows the code and length of each truncated Rg2ENO1 promoters.
Figure 5:
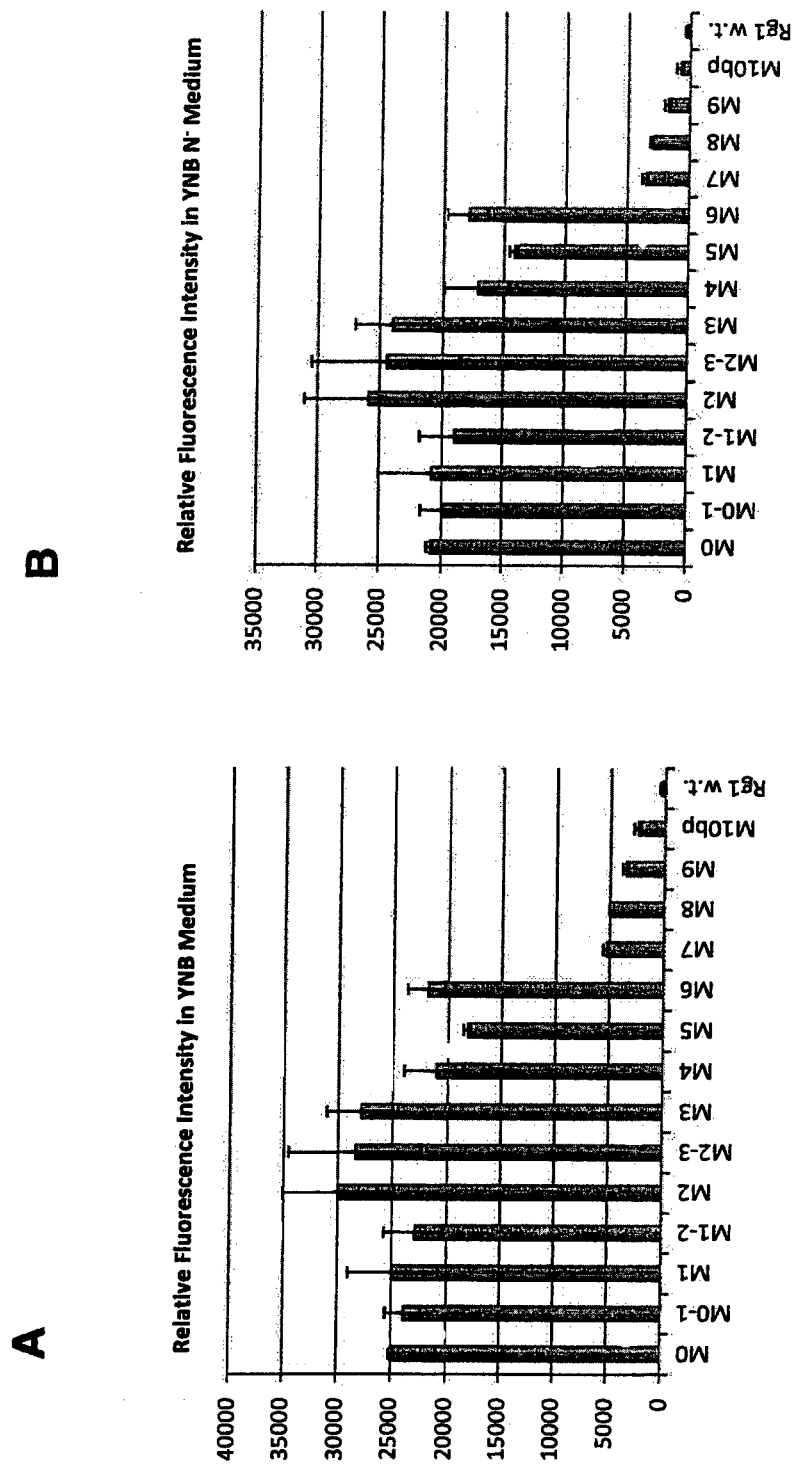
FIG. 5A and FIG. 5B show the relative florescence of RtGFP driven by ENO1 promoters of various lengths, which is defined as the nucleotide number starting from the first nucleotide from the putative translation initiation codon (ATG) up to the point of 5' end, excluding the restriction sites added. The promoters showed similar trend in YNB (FIG. 5A) and YNB nitrogen-free ($N^{31}$) (FIG. 5B) media. Rg1 Wt refers to the background florescence of *R. glutinis* ATCC 90781.

Primers were designed at various locations in the 519 bp Rg2ENO1 promoter sequence, which were used for PCR in combination with the reverse primer targeting the 3' end of the promoter (FIG. 4A). All 5' primers included a SpeI cutting site while the 3' primer contains a NcoI cutting site. The lengths of the PCR products (excluding the extra linker sequence at 5' end and the ATG codon at the 3' site) are summarized in FIG. 4B. The PCR fragments were individually digested with SpeI and NcoI and cloned in pRH2031-Rg2ENO1-RtGFP at the same sites, replacing the full-length ENO1 promoter. Constructs were transformed by the ATMT method to *Rhodotorula glutinis* ATCC 90781, which is the diploid parent of *Rhodosporidium toruloides* ATCC 10657 and ATCC 10788. The transformed colonies (>500) were pooled, cultured in YNB medium with 150 μg/ml hygromycin B and 300 μg/ml cefataxome for 2 days at 28° C. and diluted to about 0.1 $OD_{600}$ in YNB Medium and also in YNB N⁻ Medium (both medium with 5% glucose.) and continued culture for 12 hours with shaking. The cultures reached $OD_{600}$ 0.5~0.7 in YNB and YNB N⁻ meda. GFP florescence was measured with Tecan infinite M200. Gain parameter is consistently set at 85; Excitation and Emission wavelength are 476, 509. The GFP fluorescence intensity (normalized against the OD600) is listed in FIGS. 5A and 5B. The promoter showed similar trends in the two media tested. The biggest drop in activity was seen promoter M6 and M7. Another significant drop was observed between M3 and M6, where several GAGGAG-related motifs can be found (FIG. 4A).

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or clearly contradicted by context.

The term "efficient expression" refers to expression of a reporter protein to a level that is detectable for fluormetry, photomicrospy or phenotypic selection of transformants by antibiotics, such as hygromycin.

BIBLIOGRAPHY

An, G., et al., 1989. Functional analysis of the 3' control region of the potato wound-inducible proteinase inhibitor II gene. Plant Cell, 1: 115-122.

Bassett, C. L., 2007. Regulation of Gene Expression in Plants: The Role of Transcript Structure and Processing. New York: Springer Press.

Bölker, M., et al., 1995. Tagging pathogenicity genes in *Ustilago maydis* by restriction enzyme-mediated integration (REMI). Mol Gen Genet. 248, 547-52.

Boulton, S., et al., 1999. Interactive effects of inhibitors of poly(ADP-ribose) polymerase and DNA-dependent protein kinase on cellular responses to DNA damage. Carcinogenesis. 20, 199-203.

Boulton, S., et al., 1996. Wortmannin is a potent inhibitor of DNA double strand break but not single strand break repair in Chinese hamster ovary cells. Carcinogenesis. 17, 2285-90.

Bundock, P., et al., 1995. Trans-kingdom T-DNA transfer from *Agrobacterium tumefaciens* to *Saccharomyces cerevisiae*. EMBO J. 14, 3206-14.

Choi, J., et al., 2007. Genome wide analysis of T DNA integration into the chromosomes of *Magnaporthe oryzae*. Molecular Microbiology. 66, 371-382.

Comai, L., et al., 1983. An altered aroA gene product confers resistance to the herbicide glyphosate. Science. 221, 370.

De Groot, M. J. A., et al., 1998. *Agrobacterium tumefaciens*-mediated transformation of filamentous fungi. Nature Biotechnology. 16, 839-842.

de Oliveira, M. L. P., et al., 2009. High-efficiency *Agrobacterium*-mediated transformation of citrus via sonication and vacuum infiltration. Plant Cell Reports. 28, 387-395.

Durant, S., Karran, P., 2003. Vanillins—a novel family of DNA-PK inhibitors. Nucleic Acids Res. 31, 5501-12.

Gietz, R. D. and Woods, R. A., 2002. Transformation of yeast by lithium acetate/single-stranded carrier DNA/polyethylene glycol method. Methods Enzymol. 350, 87-96.

Goldstein, A. L. and McCusker, J. H., 1999. Three new dominant drug resistance cassettes for gene disruption in *Saccharomyces cerevisiae*. Yeast. 15, 1541-1553.

Gutiérrez, R. A., et al., 1999. Current perspectives on mRNA stability in plants: multiple levels and mechanisms of control. Trends Plant Sci, 4: 429-438.

Hajdukiewicz, P., et al., 1994. The small, versatilepPZP family of *Agrobacterium* binary vectors for plant transformation. Plant Molecular Biology. 25, 989-994.

Haughn, G. W., et al., 1988. Transformation with a mutant *Arabidopsis* acetolactate synthase gene renders tobacco resistant to sulfonylurea herbicides. Molecular and General Genetics. 211, 266-271.

Heiser, W. C., 2000. Optimizing electroporation conditions for the transformation of mammalian cells. Methods in Molecular Biology. 130, 117-34.

Hentges, P., et al., 2005. Three novel antibiotic marker cassettes for gene disruption and marker switching in *Schizosaccharomyces pombe*. Yeast. 22, 1013-9.

Hewald, S., et al., 2005. Genetic analysis of biosurfactant production in *Ustilago maydis*. Applied and Environmental Microbiology. 71, 3033.

Hill, J., et al., 1991. DMSO-enhanced whole cell yeast transformation. Nucleic Acids Research. 19, 5791.

Ho, Eric C H, et al (2007). Gene discovery and transcript analyses in the corn smut pathogen *Ustilago maydis*: expressed sequence tag and genome sequence comparison. BMC genomics 8:334.

Horns, F., et al. 2012. Patterns of repeat-induced point mutation in transposable elements of basidiomycete fungi. *Genome biology and evolution*, 4, 240-247.

Hu, C., et al., 2009. Effects of biomass hydrolysis by-products on oleaginous yeast *Rhodosporidium toruloides*. Bioresour Technol. 100, 4843-7.

Ianiri, G., et al., 2011. Development of resources for the analysis of gene function in Pucciniomycotina red yeasts. Fungal Genetics and Biology. 48, 685-695.

Ingelbrecht, I. L., et al., 1989. Different 3' end regions strongly influence the level of gene expression in plant cells. Plant Cell, 1: 671-680.

Ito, H., et al., 1983. Transformation of intact yeast cells treated with alkali cations. Journal of bacteriology. 153, 163-8.

Ji, L., et al., 2010. A Simplified and efficient method for transformation and gene tagging of *Ustilago maydis* using frozen cells. Fungal Genet Biol. 47, 279-87.

Käamper, J., 2004. A PCR-based system for highly efficient generation of gene replacement mutants in *Ustilago maydis*. Mol Genet Genomics. 271, 103-10.

Khanna, H. K., et al., 2007. Inhibition of *Agrobacterium*-induced cell death by antiapoptotic gene expression leads to very high transformation efficiency of banana. Molecular Plant-Microbe Interactions. 20, 1048-1054.

Kirk, M. P., et al. Dictionary of the Fungi. CABI, Wallingford, 2008, pp. 716.

Krugel, H., et al., 1988. Analysis of the nourseothricin-resistance gene (nat) of *Streptomyces noursei*. Gene. 62, 209-217.

Kück, U. and Hoff, B., 2010. New tools for the genetic manipulation of filamentous fungi. Appl Microbiol Biotechnol. 86, 51-62.

Kuo, C. Y., et al., 2004. Cloning of glyceraldehyde-3-phosphate dehydrogenase gene and use of the gpd promoter for transformation in *Flammulina velutipes*. Appl Microbiol Biotechnol. 65, 593-9.

Lazo, G. R., et al., 1991. A DNA transformation-competent *Arabidopsis* genomic library in *Agrobacterium*. Biotechnology (N Y). 9, 963-7.

Liu, Y. G., Chen, Y., 2007. High-efficiency thermal asymmetric interlaced PCR for amplification of unknown flanking sequences. BioTechniques. 43, 649-50, 652, 654 passim.

Liu et al, 2012, Characterization of glyceraldehyde-3-phosphate dehydrogenase gene RtGPD1 and development of genetic transformation method by dominant selection in oleaginous yeast *Rhodosporidium toruloides*. Applied Microbiology and Biotechnology. 10.1007/s00253-012-4223-9.

Liu, Y. G., Whittier, R. F., 1995. Thermal asymmetric interlaced PCR: automatable amplification and sequencing of insert end fragments from P1 and YAC clones for chromosome walking. Genomics. 25, 674-81.

Maehara, T., et al., 2010. Improvement of the Transformation Efficiency of *Flammulina velutipes* Fv-1 Using the Glyceraldehyde-3-phosphate Dehydrogenase Gene Promoter. Bioscience, Biotechnology, and Biochemistry. 74, 2523-2525.

Maier, F. J., Schafer, W., 1999. Mutagenesis via insertional- or restriction enzyme-mediated-integration (REMI) as a tool to tag pathogenicity related genes in plant pathogenic fungi. Biol Chem. 380, 855-64.

Meng, X., et al., 2009. Biodiesel production from oleaginous microorganisms. Renewable Energy. 34, 1-5.

Meyer, V., 2008. Genetic engineering of filamentous fungi—Progress, obstacles and future trends. Biotechnology Advances. 26, 177-185.

Meyer, V., et al., 2003. Comparison of different transformation methods for *Aspergillus giganteus*. Curr Genet. 43, 371-7.

Mogen, B. D., et al., 1990. Upstream sequences other than AAUAAA are required for efficient messenger RNA 3'-end formation in plants. Plant Cell, 2: 1261-1272.

Mogen, B. D., et al., 1992. Several distinct types of sequence elements are required for efficient mRNA 3' end formation in a pea rbcS gene. Molecular and Cellular Biology, 12: 5406-5414.

Nagaya, S., et al., 2010. The HSP terminator of *Arabidopsis thaliana* Increases Gene Expression in Plant Cells. Plant Cell Physiol, 51: 328-332.

Newman, T. C., et al., 1993. DST sequences, highly conserved among plant SAUR genes, target reporter transcripts for rapid decay in tobacco. Plant Cell, 5: 701-14.

Ochman, H., et al., 1988. Genetic applications of an inverse polymerase chain reaction. Genetics. 120, 621-3.

Ohme-Takagi, M., et al., 1993. The effect of sequences with high AU content on mRNA stability in tobacco. Proc Natl Acad Sci USA, 90: 11811-5.

Pfeifer, T. A., et al., 1997. Baculovirus immediate-early promoter-mediated expression of the Zeocin™ resistance gene for use as a dominant selectable marker in Dipteran and Lepidopteran insect cell lines. Gene. 188, 183-190.

Punt, P. J., et al., 1987. Transformation of *Aspergillus* based on the hygromycin B resistance marker from *Escherichia coli*. Gene. 56, 117-124.

Rosenzweig, K. E., et al., 1997. Radiosensitization of human tumor cells by the phosphatidylinositol3-kinase inhibitors wortmannin and LY294002 correlates with inhibition of DNA-dependent protein kinase and prolonged G2-M delay. Clin Cancer Res. 3, 1149-56.

Rothnie, H. M., et al., 1994. The contribution of AAUAAA and the upstream element UUUGUA to the efficiency of mRNA 3'-end formation in plants. EMBO (Eur Mol Biol Organ) J, 13: 2200-2210.

Schulz, B., et al., 1990. The b alleles of *U. maydis*, whose combinations program pathogenic development, code for polypeptides containing a homeodomain-related motif. Cell. 60, 295-306.

Scorer, C. A., et al., 1994. Rapid Selection Using G418 of High Copy Number Transformants of *Pichia pastoris* for High level Foreign Gene Expression. Nature Biotechnology. 12, 181-184.

Skalitzky, D. J., et al., 2003. Tricyclic benzimidazoles as potent poly(ADP-ribose) polymerase-1 inhibitors. J Med Chem. 46, 210-3.

Smith, G. and Jackson, S., 1999. The DNA-dependent protein kinase. Genes & development. 13, 916.

Smith, T. L. and Leong, S. A., 1990. Isolation and characterization of a *Ustilago maydis* glyceraldehyde-3-phosphate dehydrogenase-encoding gene. Gene. 93, 111-7.

Soltani, J., et al., *Agrobacterium*-mediated transformation of non-plant organisms. In: T. Tzfira, V. Citovsky, Eds.), *Agrobacterium*: from biology to biotechnology. Springer press, New York, USA, 2008, pp. 649-675.

Spellig, T., et al., 1996. Green fluorescent protein (GFP) as a new vital marker in the phytopathogenic fungus *Ustilago maydis*. Mol Gen Genet. 252, 503-9.

Steiner, S. and Phillippsen P, 1994. Sequence and promoter analysis of the highly expressed TEF gene of the filamentous fungus *Ashbya gossypii*. Mol Gen Genet 242, 263-271.

Sweigard, J. A., et al., 1998. *Magnaporthe grisea* pathogenicity genes obtained through insertional mutagenesis. Mol Plant Microbe Interact. 11, 404-12.

Takeno, S., et al., 2005. Transformation of oil-producing fungus, *Mortierella alpina* 1S-4, using Zeocin, and application to arachidonic acid production. Journal of bioscience and bioengineering. 100, 617-622.

Teichmann, B., et al., 2010. Molecular characterization of the biocontrol activity of *Pseudozyma flocculosa*. Phytopathology. 100.

Tentori, L., et al., 2002. Potential clinical applications of poly(ADP-ribose) polymerase (PARP) inhibitors. Pharmacol Res. 45, 73-85.

Tully, M. and Gilbert, H. J., 1985. Transformation of *Rhodosporidium toruloides*. Gene. 36, 235-40.

Turgeon, B. G., et al., 2010. Protoplast transformation of filamentous fungi. Methods in molecular biology. 638, 3-19.

van Attikum, H., et al., 2001. Non-homologous end joining proteins are required for *Agrobacterium* T-DNA integration. Embo J. 20, 6550-8.

van Attikum, H., et al., 2003. The *Arabidopsis* AtLIG4 gene is required for the repair of DNA damage, but not for the integration of *Agrobacterium* T-DNA. Nucleic Acids Res. 31, 4247-55.

Vega, J. M., et al., 2008. Improvement of *Agrobacterium*-mediated transformation in Hi-II maize (*Zea mays*) using standard binary vectors. Plant cell reports. 27, 297-305.

Veuger, S. J., et al., 2003. Radiosensitization and DNA repair inhibition by the combined use of novel inhibitors of DNA-dependent protein kinase and poly(ADP-ribose) polymerase-1. Cancer Res. 63, 6008-15.

Willmore, E., et al., 2004. A novel DNA-dependent protein kinase inhibitor, NU7026, potentiates the cytotoxicity of topoisomerase II poisons used in the treatment of leukemia. Blood. 103, 4659-65.

Wu, S. and Letchworth, G. J., 2004. High efficiency transformation by electroporation of *Pichia pastoris* pretreated with lithium acetate and dithiothreitol. BioTechniques. 36, 152-155.

Wu, S., et al., 2010a. Phosphate-limitation mediated lipid production by *Rhodosporidium toruloides*. Bioresour Technol. 101, 6124-9.

Wu, S., et al., 2010b. Microbial lipid production by *Rhodosporidium toruloides* under sulfate-limited conditions. Bioresour Technol.

Ye, X. and Gilbertson, L., use of multiple transformation enhancer sequences to improve plant transformation efficiency. EP Patent 2,038,420, 2009.

Zhao, X., et al., 2010a. Lipid production by *Rhodosporidium toruloides* Y4 using different substrate feeding strategies. J Ind Microbiol Biotechnol.

Zhao, X., et al., 2010b. Lipid production from Jerusalem artichoke by *Rhodosporidium toruloides* Y4. J Ind Microbiol Biotechnol. 37, 581-5.

Zhu, Z., et al, 2012, A multi-omic map of the lipid-producing yeast *Rhodosporidium toruloides*, Nature Communications, 3, 1112.

---

What is claimed is:

1. A transgenic fungal cell containing at least one DNA construct which comprises an isolated nucleotide sequence selected from SEQ ID NO:6 or 8 or promoter portion thereof operatively linked to a heterologous polypeptide-encoding sequence operatively linked to a transcriptional terminator, wherein the fungal cell expresses the heterologous polypeptide and wherein the fungal cell is a cell of a fungal species selected from *Rhodosporidium*, *Rhodotorula*, *Pseudozyma*, *Ustilago* or *Sporobolomyces* genus.

2. The transgenic fungal cell of claim 1, wherein the polypeptide-encoding sequence contains at least 50% CG.

3. The transgenic fungal cell of claim 1, wherein the cell contains no more than 2 identical copies of a nucleotide sequence set forth in SEQ ID NO 6 or 8 or promoter portion thereof.

4. The transgenic fungal cell of claim 3, wherein the promoter portion is about 400 base pairs up to about 1100 base pairs in length starting from the −1 position from the ATG codon.

5. The transgenic fungal cell of claim 1, wherein the polypeptide-encoding sequence contains more than 60% CG.

6. The transgenic fungal cell of claim 1, wherein the polypeptide-encoding sequence contains more than 70% CG.

7. The transgenic fungal cell of claim 1, wherein the polypeptide-encoding sequence contains more than 80% CG.

8. The transgenic fungal cell of claim 1, wherein the cell contains no more than 3 identical copies of a nucleotide sequence set forth in SEQ ID NO:6 or 8 or promoter portion thereof.

9. The transgenic fungal cell of claim 8, wherein the promoter portion is about 400 base pairs up to about 1100 base pairs in length starting from the −1 position from the ATG codon.

10. A recombinant T-DNA vector or a recombinant shuttle vector comprising a DNA construct which comprises an isolated nucleotide sequence selected from SEQ ID NO:6 or 8 or promoter portion thereof operatively linked to a heterologous polypeptide-encoding sequence operatively linked to a transcriptional terminator, wherein the DNA construct enables efficient expression of the heterologous polypeptide in a fungal cell of a fungal species selected from *Rhodosporidium, Rhodotorula, Pseudozyma, Ustilago* or *Sporobolomyces* genus.

11. The recombinant T-DNA vector or recombinant shuttle vector of claim 10, wherein the promoter portion is about 400 base pairs up to about 1100 base pairs in length starting from the −1 position from the ATG codon.

12. A recombinant fungal chromosome comprising a DNA construct which comprises an isolated nucleotide sequence selected from SEQ ID NO:6 or 8 or promoter portion thereof operatively linked to a heterologous polypeptide-encoding sequence operatively linked to a transcriptional terminator, wherein the DNA construct enables efficient expression of the heterologous polypeptide in a fungal cell of a fungal species selected from *Rhodosporidium, Rhodotorula, Pseudozyma, Ustilago* or *Sporobolomyces* genus.

13. The recombinant fungal chromosome of claim 12, wherein the promoter portion is about 400 base pairs up to about 1100 base pairs in length starting from the −1 position from the ATG codon.

* * * * *